US007135551B2

(12) United States Patent
Wei et al.

(10) Patent No.: US 7,135,551 B2
(45) Date of Patent: Nov. 14, 2006

(54) CHEMOKINE β-15

(75) Inventors: Ying-Fei Wei, Berkeley, CA (US);
Brent L Kreider, Bedford, MA (US);
Craig A Rosen, Laytonsville, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 693 days.

(21) Appl. No.: 10/263,766

(22) Filed: Oct. 4, 2002

(65) Prior Publication Data
US 2003/0073198 A1 Apr. 17, 2003

Related U.S. Application Data

(60) Division of application No. 09/272,162, filed on Mar. 19, 1999, now Pat. No. 6,503,735, which is a continuation of application No. 08/874,460, filed on Jun. 16, 1997, now Pat. No. 5,981,231.

(60) Provisional application No. 60/019,837, filed on Jun. 17, 1996.

(51) Int. Cl.
C07K 14/475 (2006.01)

(52) U.S. Cl. ..................... 530/350; 530/300; 435/69.1; 514/2; 514/12

(58) Field of Classification Search ..................... None
See application file for complete search history.

(56) References Cited

U.S. PATENT DOCUMENTS

| 5,278,287 A | 1/1994 | Rollins et al. |
| 5,306,709 A | 4/1994 | Gewirtz |
| 5,504,003 A | 4/1996 | Li et al. |
| 5,556,767 A | 9/1996 | Rosen et al. |
| 5,605,817 A | 2/1997 | Coleman et al. |

FOREIGN PATENT DOCUMENTS

| WO | WO 90/02762 | 3/1990 |
| WO | WO 92/00326 | 1/1992 |
| WO | WO 92/00327 | 1/1992 |
| WO | WO 92/05198 | 4/1992 |
| WO | WO 92/13553 | 8/1992 |
| WO | WO 93/09799 | 5/1993 |
| WO | WO 95/17092 | 6/1995 |
| WO | WO 96/16979 | 6/1996 |
| WO | WO 96/24668 | 8/1996 |
| WO | WO 98/01557 | 1/1998 |
| WO | WO 98/44117 | 10/1998 |

OTHER PUBLICATIONS

Bischoff, S.C. et al., "Monocyte Chemotactic Protein 1 Is a Potent Activator of Human Basophils," *J. Exp. Med.* 175:1271-1275 (1992).
Bischoff, S.C. et al., "RANTES and related chemokines activate human basophil granulocytes through different G protein-coupled receptors," *Eur. J. Immunol.* 23:761-767 (1993).
Chang, M.S. et al., "Cloning and Characterization of the Human Neutrophil-activating Peptide (ENA-78) Gene," *J. Biol. Chem.* 269(41):25277-25282 (1994).
Damme, J. et al., "Structural and Functional Identification of Two Human, Tumor-derived Monocyte Chemotactic Proteins (MCP-2 and MCP-3) Belonging to the Chemokine Family," *J. Exp. Med.* 176:59-65 (1992).
Fuentes, M.E. et al., "Controlled Recruitment of Mono-cytes and Macrophages to Specific Organs Through Transgenic Expression of Monocyte Chemoattractant Protein-1," *J. Immunol.* 155:5769-5776 (Dec. 1995).
Graham, G.J. and Pragnell, I.B., "SCI/MIP-1α: A Potent Stem Cell Inhibitor with Potential Roles in Development," *Devel. Biol.* 151:377-381 (1992).
Hara, T. et al., "Molecular Cloning and Functional Characterization of a Novel Member of the C-C Chemokine Family," *J. Immunol.* 155:5352-5358 (Dec. 1995).
Howard, O.M.Z. et al., "Chemokines: progress toward identifying molecular targets for therapeutic agents," *TIBTECH* 14:46-51 (Feb. 1996).
Jiang, Y. et al., "Monocyte Chemoattractant Protein-1 Regulates Adhesion Molecule Expression and Cytokine Production in Human Monocytes," *J. Immunol.* 148(8):2423-2428 (1992).
Johnson II, M.C. et al., "Cloning of two rabbit *GRO* homologues and their expression in alveolar macrophages," *Gene* 151:337-338 (1994).
Jose, P.J. et al., "Eotaxin: A Potent Eosinophil Chemoattractant Cytokine Detected in a Guinea Pig Model of Allergic Airways Inflammation," *J. Exp. Med.* 179:881-887 (1994).
Kurdowska, A. et al., "Biological and Kinetic Characterization of Recombinant Human Macrophage Inflammatory Peptides 2 Alpha and Beta and Comparison with the Neutrophil Activating Peptide 2 and Interleukin 8," *Cytokine* 6(2):124-134 (1994).
Lukacs, N.W. et al., "The Role of Macrophage Inflammatory Protein 1α in *Sachistosoma mansoni* Egg-induced Granulomatous Inflammation," *J. Exp. Med.* 177:1551-1559 (1993).
Luo, Y. et al., "Biologic Activities of the Murine β-Chemokine TCA3," *J. Immunol.* 153:4616-4624 (1994).
McColl, S.R. et al., "Uncoupling of Early Signal Transduction Events from Effector Function in Human Peripheral Blood Neutrophils in Response to Recombinant Macrophage Inflammatory Proteins-1α and -1β," *J. Immunol.* 150:4550-4560 (1993).
Miller, M.D. and Krangel, M.S., "Biology and Biochemistry of the Chemokines: A Family of Chemotactic and Inflammatory Cytokines," *Crit. Rev. Immunol.* 12(1,2):17-46 (1992).

(Continued)

Primary Examiner—Elizabeth Kemmerer
(74) Attorney, Agent, or Firm—Human Genome Sciences, Inc.

(57) ABSTRACT

The present invention concerns a member of the human chemokine CC protein family. In particular, isolated nucleic acid molecules are provided encoding the chemokine β-15 protein. Chemokine β-15 polypeptides are also provided. The invention further concerns diagnostic methods for detecting thymus disorders and therapeutic methods for modulating bone marrow cell proliferation and differentiation.

28 Claims, 5 Drawing Sheets

OTHER PUBLICATIONS

Minty, A. et al., "Molecular cloning of the MCP-3 chemokine gene and regulation of its expression," *Eur. Cytokine Netw.* 4(2):99-110 (1993).

Opdenakker, G. et al., "Human monocyte chemotactic protein-3 (MCP-3): molecular cloning of the cDNA and comparison with other chemokines," *Biochem. Biophys. Res. Comm.* 191(2):535-542 (1993).

Poltorak, A. et al., "Molecular Cloning of MIP-1γ, A New Member of the Chemokine Family, Through Differential Screening Based on Extinction of Macrophage-Specific Genes," *Clin. Res.* 42(2):306A (1994).

Power, C.A. et al., "Cloning of a full-length cDNA encoding the neutrophil-activating peptide ENA-78 from human platelets," *Gene* 151:333-334 (1994).

Proost, P. et al., "Human and Bovine Granulocyte Chemotactic Protein-2: Complete Amino Acid Sequence and Functional Characterization as Chemokines," *Biochemistry* 32:10170-10177 (1993).

Proost, P. et al., "Purification, Sequence Analysis, and Biological Characterization of a Second Bovine Monocyte Chemotactic Protein-1 (Bo MCP-1B)," *Biochemistry* 33:13406-13412 (1994).

Proudfoot, A.E.I. et al., "Extension of Recombinant Human RANTES by the Retention of the Initiating Methionine Produces a Potent Antagonist," *J. Biol. Chem.* 271(5):2599-2603 (Feb. 1996).

Schulz-Knappe, P. et al., "HCC-1, a Novel Chemokine from Human Plasma," *J. Exp. Med.* 183:295-299 (Jan. 1996).

Proost, P. et al., "Purification, Sequence Analysis, and Biological Characterization of a Second Bovine Monocyte Chemotactic Protein-1 (Bo MCP-1B)," *Biochemistry* 33:13406-13412 (1994).

Yoshida, T. et al., "Molecular cloning of a novel C or γ type chemokine, SCM-1," *FEBS Lett.* 360:155-159 (Feb. 1995).

Youn, B.S. et al., "A novel chemokine, microphage inflammatory protein-related protein-2, inhibits colony formation of bone marrow myeloid progenitors," J. Immunol. 155(5):2661-2667 (1995).

International Search Report for WO Application No. PCT/US95/09058 (Mailing Date: Oct. 19, 1995).

Adams, M.D. et al., "Initial assessment of human gene diversity and expression patterns based upon 83 million nucleotides of cDNA sequence," *Nature* 377:3-174 (1995).

Hillier, L. et al., Accession No. N73958 (Mar. 1996).

Kennedy, J. et al., "Molecular Cloning and Functional Characterization of Human Lymphotactin," *J. Immunol.* 155:203-209, American Association of Immunologists (1995).

Loster, A.D., and Leder, P., "IP-10, a-C-X-C- Chemokine, Elicits a Potent Thymus-dependent Antitumor Response In Vivo," *J. Exp. Med.* 178:1057-1065, Rockefeller University Press (1993).

Meyer, A. et al., "Cloning and Characterization of a Novel Murine Macrophage Inflammatory Protein-1α Receptor," *J. Bio. Chem.* 271:14445-14451, American Society for Biochemistry and Molecular Biology, Inc. (1996).

Ngo et al., The Protein Foliding Problem and Teriary Structure Prediction. pp. 492-495. Birkhauser, Boston, (1994).

Robson, et al., Introduction to Proteins and Protein Engineering. Elsevier, Amsterdam, (1986).

Wells, Biochemistry, vol. 29, No. 37, pp. 8509-8517, (1990).

Bowie, et al., Science, vol. 247, pp. 1306-1310, (1990).

```
        -80                    -60                   -40
         .                      .                     .
CCGGCGGGCATCAGCTCCCTTGACCCAGTGGATATCGGTGGCCCCGTTATTCGTCCAGGT
------+---------+---------+---------+---------+---------+---
GGCCGCCCGTAGTCGAGGGAACTGGGTCACCTATAGCCACCGGGGCAATAAGCAGGTCCA
       -20                    +1                    20
         .                      .                     .
GCCCAGGGAGGAGGACCCGCCTGCAGCATGAACCTGTGGCTCCTGGCCTGCCTGGTGGCC
------+---------+---------+---------+---------+---------+---
CGGGTCCCTCCTCCTGGGCGGACGTCGTACTTGGACACCGAGGACCGGACGGACCACCGG
                                 M  N  L  W  L  L  A  C  L  V  A
        40                     60                    80
         .                      .                     .
GGCTTCCTGGGAGCCTGGGCCCCCGCTGTCCACACCCAAGGTGTCTTTGAGGACTGCTGC
------+---------+---------+---------+---------+---------+---
CCGAAGGACCCTCGGACCCGGGGGCGACAGGTGTGGGTTCCACAGAAACTCCTGACGACG
 G  F  L  G  A  W  A  P  A  V  H  T  Q  G  V  F  E  D  C  C
        100                    120                   140
         .                      .                     .
CTGGCCTACCACTACCCCATTGGGTGGGCTGTGCTCCGGCGCGCCTGGACTTACCGGATC
------+---------+---------+---------+---------+---------+---
GACCGGATGGTGATGGGGTAACCCACCCGACACGAGGCCGCGCGGACCTGAATGGCCTAG
 L  A  Y  H  Y  P  I  G  W  A  V  L  R  R  A  W  T  Y  R  I
        160                    180                   200
         .                      .                     .
CAGGAGGTGAGCGGGAGCTGCAATCTGCCTGCTGCGATATTCTACCTCCCCAAGAGACAC
------+---------+---------+---------+---------+---------+---
GTCCTCCACTCGCCCTCGACGTTAGACGGACGACGCTATAAGATGGAGGGGTTCTCTGTG
 Q  E  V  S  G  S  C  N  L  P  A  A  I  F  Y  L  P  K  R  H
        220                    240                   260
         .                      .                     .
AGGAAGGTGTGTGGGAACCCCAAAAGCAGGGAGGTGCAGAGAGCCATGAAGCTCCTGGAT
------+---------+---------+---------+---------+---------+---
TCCTTCCACACACCCTTGGGGTTTTCGTCCCTCCACGTCTCTCGGTACTTCGAGGACCTA
 R  K  V  C  G  N  P  K  S  R  E  V  Q  R  A  M  K  L  L  D
        280                    300                   320
         .                      .                     .
GCTCGAAATAAGGTTTTTGCAAAGCTCCACCACAACACGCAGACCTTCCAAGGCCCTCAT
------+---------+---------+---------+---------+---------+---
CGAGCTTTATTCCAAAAACGTTTCGAGGTGGTGTTGTGCGTCTGGAAGGTTCCGGGAGTA
 A  R  N  K  V  F  A  K  L  H  H  N  T  Q  T  F  Q  G  P  H
```

FIG. 1A

```
                340                      360                      380
       GCTGTAAAGAAGTTGAGTTCTGGAAACTCCAAGTTATCATCGTCCAAGTTTAGCAATCCC
       ------+---------+---------+---------+---------+---------+---
       CGACATTTCTTCAACTCAAGACCTTTGAGGTTCAATAGTAGCAGGTTCAAATCGTTAGGG
        A V K  K  L  S  S  G  N  S  K  L  S  S  S  K  F  S  N  P
                400                      420                      440

ATCAGCAGCAGCAAGAGGAATGTCTCCCTCCTGATATCAGCTAATTCAGGACTGTGAGCC
       ------+---------+---------+---------+---------+---------+---
       TAGTCGTCGTCGTTCTCCTTACAGAGGGAGGACTATAGTCGATTAAGTCCTGACACTCGG
        I  S  S  S  K  R  N  V  S  L  L  I  S  A  N  S  G  L  *
                460                      480                      500

GGCTCATTTCTGGGCTCCATCGGCACAGGAGGGGCCGGATCTTTCTCCGATAAAACCGTC
       ------+---------+---------+---------+---------+---------+---
       CCGAGTAAAGACCCGAGGTAGCCGTGTCCTCCCCGGCCTAGAAAGAGGCTATTTTGGCAG
                520                      540                      560

GCCCTACAGACCCAGCTGTCCCCACGCCTCTGTCTTTTGGGTCAAGTCTTAATCCCTGCA
       ------+---------+---------+---------+---------+---------+---
       CGGGATGTCTGGGTCGACAGGGGTGCGGAGACAGAAAACCCAGTTCAGAATTAGGGACGT
                580                      600                      620

CCTGAGTTGGTCCTCCCTCTGCACCCCCACCACCTCCTGCCCGTTTGGCAACTGGAAAGA
       ------+---------+---------+---------+---------+---------+---
       GGACTCAACCAGGAGGGAGACGTGGGGGTGGTGGAGGACGGGCAAACCGTTGACCTTTCT
                640                      660                      680

GGGAGTTGGCCTGATTTTAAGCCTTTTGCCGCTCCGGGGACCAGCAGCAATCCTGGGCAG
       ------+---------+---------+---------+---------+---------+---
       CCCTCAACCGGACTAAAATTCGGAAAACGGCGAGGCCCCTGGTCGTCGTTAGGACCCGTC
                700                      720                      740

CCAGTGGCTCTTGTAGAGAAGACTTAGGATACCTCTCTCACTTTCTGTTTCTTGCCGTCC
       ------+---------+---------+---------+---------+---------+---
       GGTCACCGAGAACATCTCTTCTGAATCCTATGGAGAGAGTGAAAGACAAAGAACGGCAGG
                760                      780                      800

ACCCCGGGCCATGCCAGTGTGTCCCTCTGGGTCCCTCCAAAACTCTGGTCAGTTCAAGGA
       ------+---------+---------+---------+---------+---------+---
       TGGGGCCCGGTACGGTCACACAGGGAGACCCAGGGAGGTTTTGAGACCAGTCAAGTTCCT
```

FIG. 1B

```
             820                    840                     860
              .                      .                       .            .
TGCCCCTCCCAGGCTATGCTTTTCTATAACTTTTAAATAAACCTTGGGGGGGTGATGGAGT
------+---------+---------+---------+---------+---------+---
ACGGGGAGGGTCCGATACGAAAAGATATTGAAAATTTATTTGGAACCCCCCACTACCTCA
        880                   900
         .                     .                 .
CAAAAAAAAAAAAAAAAAAAAAAAAAAAAAAA
------+---------+---------+---
GTTTTTTTTTTTTTTTTTTTTTTTTTTTTTTT
```

FIG. 1C

```
CKB-15  11 AGFLGAWAPAVHTQGVFE............DCCLAYHYPIGWAVLRRAWT 48
           |.   . ...:..|..:|           ||||.|: .|. .  :   :.
MMRP2    5 ATETKEVQSSLKAQQGLEIEMFHMGFQDSSDCCLSYNSRIQCSRFIGYFP 54

CKB-15  49 YRIQEVSGSCNLPAAIFYLPKRHRKVCGNPKSREVQRAMKLLDARNKVFA 98
            :||:|. | :|:::.||  .||:||..| |||.         :.
MMRP2   55 .....ISGGCTRP.GIIFISKRGFQVCANPSDRRVQRC.........IE 88

CKB-15  99 KLHHNTQTFQGPHAVKK 115
            :|.:|.|    |:. |.
MMRP2   89 RLEQNSQ....PRTYKQ 101
```

FIG. 2 ns

SEQUENCE LISTING (1) GENERAL INFORMATION:

(iii) NUMBER OF SEQUENCES: 9

(2) INFORMATION FOR SEQ ID NO: 1:

(i) SEQUENCE CHARACTERISTICS:
      (A) LENGTH: 989 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 88..534

(ix) FEATURE:
   (A) NAME/KEY: sig_peptide
   (B) LOCATION: 88..147

(ix) FEATURE:
   (A) NAME/KEY: mat_peptide
   (B) LOCATION: 148..534

(xi) SEQUENCE DESCRIPTION: SEQ ID NO: 1:

```
CCGGCGGGCA TCAGCTCCCT TGACCCAGTG GATATCGGTG GCCCCGTTAT TCGTCCAGGT      60

GCCCAGGGAG GAGGACCCGC CTGCAGC ATG AAC CTG TGG CTC CTG GCC TGC         111
                              Met Asn Leu Trp Leu Leu Ala Cys
                                  -20                 -15

CTG GTG GCC GGC TTC CTG GGA GCC TGG GCC CCC GCT GTC CAC ACC CAA       159
Leu Val Ala Gly Phe Leu Gly Ala Trp Ala Pro Ala Val His Thr Gln
        -10                 -5                  1

GGT GTC TTT GAG GAC TGC TGC CTG GCC TAC CAC TAC CCC ATT GGG TGG       207
Gly Val Phe Glu Asp Cys Cys Leu Ala Tyr His Tyr Pro Ile Gly Trp
    5                   10                  15                  20

GCT GTG CTC CGG CGC GCC TGG ACT TAC CGG ATC CAG GAG GTG AGC GGG       255
Ala Val Leu Arg Arg Ala Trp Thr Tyr Arg Ile Gln Glu Val Ser Gly
                25                  30                  35

AGC TGC AAT CTG CCT GCT GCG ATA TTC TAC CTC CCC AAG AGA CAC AGG       303
Ser Cys Asn Leu Pro Ala Ala Ile Phe Tyr Leu Pro Lys Arg His Arg
            40                  45                  50

AAG GTG TGT GGG AAC CCC AAA AGC AGG GAG GTG CAG AGA GCC ATG AAG       351
Lys Val Cys Gly Asn Pro Lys Ser Arg Glu Val Gln Arg Ala Met Lys
        55                  60                  65

CTC CTG GAT GCT CGA AAT AAG GTT TTT GCA AAG CTC CAC CAC AAC ACG       399
Leu Leu Asp Ala Arg Asn Lys Val Phe Ala Lys Leu His His Asn Thr
    70                  75                  80

CAG ACC TTC CAA GGC CCT CAT GCT GTA AAG AAG TTG AGT TCT GGA AAC       447
Gln Thr Phe Gln Gly Pro His Ala Val Lys Lys Leu Ser Ser Gly Asn
85                  90                  95                  100

TCC AAG TTA TCA TCG TCC AAG TTT AGC AAT CCC ATC AGC AGC AGC AAG       495
Ser Lys Leu Ser Ser Ser Lys Phe Ser Asn Pro Ile Ser Ser Ser Lys
                105                 110                 115

AGG AAT GTC TCC CTC CTG ATA TCA GCT AAT TCA GGA CTG TGAGCCGGCT        544
Arg Asn Val Ser Leu Leu Ile Ser Ala Asn Ser Gly Leu
            120                 125

CATTTCTGGG CTCCATCGGC ACAGGAGGGC CGGATCTTTC TCCGATAAAA CCGTCGCCCT     604

ACAGACCCAG CTGTCCCCAC GCCTCTGTCT TTTGGGTCAA GTCTTAATCC CTGCACCTGA     664

GTTGGTCCTC CCTCTGCACC CCCACCACCT CCTGCCCGTC TGGCAACTGG AAAGAGGGAG     724

TTGGCCTGAT TTTAAGCCTT TGCCGCTCC GGGGACCAGC AGCAATCCTG GGCAGCCAGT      784

GGCTCTTGTA GAGAAGACTT AGGATACCTC TCTCACTTTC TGTTTCTTGC CGTCCACCCC     844

GGGCCATGCC AGTGTGTCCC TCTGGGTCCC TCCAAAACTC TGGTCAGTTC AAGGATGCCC     904

CTCCCAGGCT ATGCTTTTCT ATAACTTTTA AATAAACCTT GGGGGGTGAT GGAGTCAAAA     964

AAAAAAAAAA AAAAAAAAAA AAAAA                                          989
```

(2) INFORMATION FOR SEQ ID NO: 2:

(i) SEQUENCE CHARACTERISTICS:
      (A) LENGTH: 149 amino acids
      (B) TYPE: amino acid
      (D) TOPOLOGY: linear (ii) MOLECULE TYPE: protein (xi) SEQUENCE DESCRIPTION: SEQ ID NO: 2:

```
Met Asn Leu Trp Leu Leu Ala Cys Leu Val Ala Gly Phe Leu Gly Ala
-20              -15              -10                        -5

Trp Ala Pro Ala Val His Thr Gln Gly Val Phe Glu Asp Cys Cys Leu
            1                5                   10

Ala Tyr His Tyr Pro Ile Gly Trp Ala Val Leu Arg Arg Ala Trp Thr
        15                  20                  25

Tyr Arg Ile Gln Glu Val Ser Gly Ser Cys Asn Leu Pro Ala Ala Ile
        30                  35                  40

Phe Tyr Leu Pro Lys Arg His Arg Lys Val Cys Gly Asn Pro Lys Ser
45              50                  55                      60

Arg Glu Val Gln Arg Ala Met Lys Leu Leu Asp Ala Arg Asn Lys Val
                65                  70                  75

Phe Ala Lys Leu His His Asn Thr Gln Thr Phe Gln Gly Pro His Ala
                80                  85                  90

Val Lys Lys Leu Ser Ser Gly Asn Ser Lys Leu Ser Ser Ser Lys Phe
            95                  100                 105

Ser Asn Pro Ile Ser Ser Ser Lys Arg Asn Val Ser Leu Leu Ile Ser
        110                 115                 120

Ala Asn Ser Gly Leu
125
```

(2) INFORMATION FOR SEQ ID NO: 3:

(i) SEQUENCE CHARACTERISTICS:
        (A) LENGTH: 95 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 3:

```
Ala Thr Glu Thr Lys Glu Val Gln Ser Ser Leu Lys Ala Gln Gln Gly
1               5                   10                  15

Leu Glu Ile Glu Met Phe His Met Gly Phe Gln Asp Ser Ser Asp Cys
            20                  25                  30

Cys Leu Ser Tyr Asn Ser Arg Ile Gln Cys Ser Arg Phe Ile Gly Tyr
        35                  40                  45

Phe Pro Ile Ser Gly Gly Cys Thr Arg Pro Gly Ile Ile Phe Ile Ser
    50                  55                  60

Lys Arg Gly Phe Gln Val Cys Ala Asn Pro Ser Asp Arg Arg Val Gln
65              70                  75                      80

Arg Cys Arg Leu Glu Gln Asn Ser Gln Pro Arg Thr Tyr Lys Gln
                85                  90                  95
```

(2) INFORMATION FOR SEQ ID NO: 4:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 4:

GCCGTCGACG TCCACACCCA AGGTGTC                                        27

(2) INFORMATION FOR SEQ ID NO: 5:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 5:

```
GCCTCTAGAG GAGCCCAGAA ATGAGCCGGC                              30
```

(2) INFORMATION FOR SEQ ID NO: 6:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 6:

```
GCCTCTAGAG CCATCATGAA CCTGTGGCTC CTGGCC                       36
```

(2) INFORMATION FOR SEQ ID NO: 7:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 7:

```
GCCTCTAGAG GAGCCCAGAA ATGACCCGGC                              30
```

(2) INFORMATION FOR SEQ ID NO: 8:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 8:

```
GCGAAGCTTA TGAACCTGTG GCTCCTGGCC                              30
```

(2) INFORMATION FOR SEQ ID NO: 9:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 9:

```
GCGCTCGAGT CAAGCGTAGT CTGGGACGTC GTATGGGTAC AGTCCTGAAT TAGCTGATAT    60
C                                                                   61
```

CHEMOKINE β-15

This application is a divisional of U.S. patent application Ser. No. 09/272,162, filed Mar. 19, 1999, now U.S. Pat. No. 6,503,735, which is a continuation of U.S. patent application Ser. No. 08/874,460, filed Jun. 16, 1997, now U.S. Pat. No. 5,981,231, which claims benefit under 35 U.S.C. § 119(e) of U.S. Provisional Application No. 60/019,837, filed on Jun. 17, 1996, each of which is herein incorporated by reference in their entirety.

BACKGROUND OF THE INVENTION

1. Field of the Invention

The present invention relates to a human CC chemokine protein (i.e., a cytokine having the first two of its four cysteine residues adjacent as indicated by "CC") and to polynucleotides encoding this protein.

2. Background Information

The discovery of IL-8, in 1987, revealed the existence of a novel class of small cytokines, now called chemokines, that are widely studied because of their ability to activate leukocytes and their potential role as mediators of inflammations. A number of different human chemokines have been identified after IL-8, by cloning or biochemical purification and amino acid sequencing. All have four conserved cysteines that form characteristic disulfide bonds, a short amino-terminal and a longer carboxy-terminal sequence. Two subfamilies are distinguished by the arrangement of the first two cysteines, which are either separated by one amino acid (CXC chemokines) or are adjacent (CC chemokines.). Chemokine cDNAs typically encode proteins of 92–99 amino acids in length that are secreted after cleavage of a leader sequence of 20–25 amino acids. Modeling on the basis of the NMR-derived structure of IL-8 suggests that CXC and CC chemokines are folded in a similar manner.

The first human CC chemokine was identified by differential hybridization cloning and was termed LD78 (Obaru, K. Fukuda, M., Maeda, S. and Shimada, K. (1986) J. Biochem. (Tokyo) 99, 885–894.) Several cDNA isoforms of a closely related human chemokine, Act-2, were later described (Miller, M. D. and Krangel, M. S. (1992) Crit. Rev. Immunol. 12, 17–46), and two similar proteins, macrophage inflammatory protein 1α (MIP-1α) and MIP-1β, were purified form the culture medium of lipopolysaccharide (LPS)-stimulated mouse macrophages (Wolpe, S. D., Davatelis, G. Sherry, B. et al. (1988) J. Exp. Med. 167, 570–581). On the basis of more than 70% amino acid identity, the murine and human proteins are considered as homologs, and the terms human MIP-1α and MIP-1β are commonly used instead of LD78 and Act-2. The best characterized CC chemokine is monocyte chemotactic protein 1 (MCP-1), which was purified and cloned from different sources (Miller, M. D. and Krangel, M. S. (1992) Crit. Rev. Immunol. 12, 17–46; Yoshimure, T. Robinson, E. A. Tanaka, S. Appella, E. and Leonardo, E. J. (1989) J. Immunol. 142, 1956–1962; Matsushima, K., Larsen, C. G., DuBois, G. C. and Oppenheim, J. J. (1989) J. Exp. Med. 169, 1485–1490). Other CC chemokines, I-309 (Miller, M. D., Hata, S., De Waal Malafyt, R. and Krangel, M. S. (1989) J. Immunol. 143, 2907–2916), RANTES (Schall, T. J. Jongstra, J., Dyer, B. J. et al. (1988) J. Immunol. 141, 1018–1025) and HC14 (Chang, H. C., Hsu, F., Freeman, G. J., Griffin, J. D. and Reinherz, E. L. (1989) Int. Immunol. 1, 388–397), were purified or cloned as products of activated T cells. HC14, termed MCP-2, was also isolated from osteosarcoma cell cultures (Van Damme, J. Proost, P., Lenaerts, J-P. and Opdenakker, G. (1992) J. Exp. Med. 176, 59–65), along with a novel CC chemokine, MCP-3, which was subsequently cloned and expressed (Minty, A. Chalon, P. Guillemot, J. C. et al. (1993) Eur. Cytokine Netw. 4, 99–110; Opdenakker, G. Froyen, G. Fiten, P., Proost, P. and Van Damme, J.(1993) Biochem. Biophys. Res. Commun. 1991, 535–542). These CC chemokines share a sequence identify with MCP-1 of between 29 and 71% (MCP-2 and MCP-3 have 62–71% identity with MCP-1).

MCP-1, the prototype of the CC chemokine sub-family, is chemotatic for monocytes but not for neutrophils (Yoshimure, T. Robinson, E. A. Tanaka, S. Appella, E. and Leonardo, E. J. (1989) J. Immunol. 142,1956–1962; Matsushima, K, Larsen, C. G., DuBois, G. C. and Oppenheim, J. J. (1989) J. Exp. Med. 169, 1485–1490) and was initially considered to be a counterpart of IL-8. Indeed, monocytes respond to all CC chemokines, as judged from stimulus-dependent $[Ca^{2+}]i$ changes (Miller, M. D. and Krangel, M. S. (1992) Crit. Rev. Immunol. 12, 17–46; Bioschoff, S. C., Krieger, M. Brunner, T. et al. (1993) Eur. J. Immunol. 23, 761–767; McColl, S. R., Hachicha, M., Levasseur, S., Noete, K. and Schall, T. J. (1993) J. Immunol. 150, 4550–4560). MCP-1, MCP-2 and MCP-3 induce monocyte infiltration on intradermal injection into rats and rabbits (Van Damme, J. Proost, P., Lenaerts, J-P. and Opdenakker, G. (1992) J. Exp. Med. 176, 59–65; Zacha, C, O. C., Anderson, A. O., Thompson, H. L. et al. (1990) J. Exp. Med. 171, 2177–2182), and MCP-1 also elicits in monocytes a respiratory burst (Miller, M. D. and Krangel, M. S. (1992) Crit. Rev. Immunol. 12, 17–46) and the expression of β2 integrins (Jiang, Y., Beller, D. I., Frendi, G. and Graves, D. T. (1992) J. Immunol. 148, 2423–2428).

While the view that CXC chemokines act on neutrophils and CC chemokines act on monocytes apparently remains valid, recent studies have revealed that CC chemokines have a much wider range of biological activities since they can also activate some lymphocytes and, in particular, basophil and eosinophil leukocytes. Thus, there is a continuing need in the art for isolating novel CC chemokines.

SUMMARY OF THE INVENTION

The present invention provides isolated nucleic acid molecules comprising a polynucleotide encoding a human chemokine β-15 (CKβ-15)polypeptide having the amino acid sequence in FIGS. 1A–C (SEQ ID NO:2) or the amino acid sequence encoded by the cDNA clone deposited as ATCC Deposit Number 97519 on Apr. 25, 1996. The nucleotide sequence determined by sequencing the deposited CKβ-15 cDNA clone, which is shown in FIGS. 1A–C (SEQ ID NO:1), contains an open reading frame encoding a polypeptide of about 149 amino acid residues including an initiation codon at positions 1–3, a leader sequence of about 20 amino acid residues and a deduced molecular weight of about 16 kDa. The 129 amino acid sequence of the predicted mature CKβ-15 protein is shown in FIGS. 1A–C (amino acid residues from about 21 to about 149) and in SEQ ID NO:2 (amino acid residues from about 1 to about 129).

Thus, one aspect of the invention provides isolated nucleic acid molecules comprising a polynucleotide having a nucleotide sequence selected from the group consisting of: (a) a nucleotide sequence encoding the chemokine β-15 polypeptide having the complete amino acid sequence in SEQ ID NO:2; (b) a nucleotide sequence encoding the chemokine β-15 polypeptide having the complete amino acid sequence in SEQ ID NO:2 but lacking the N-terminal methionine residue; (c) a nucleotide sequence encoding the mature chemokine β-15 polypeptide having the amino acid sequence at positions from about 1 to about 129 in SEQ ID NO:2; (d) a nucleotide sequence encoding the chemokine β-15 polypeptide having the complete amino acid sequence encoded by the cDNA clone contained in ATCC Deposit No. 97519; (e) a nucleotide sequence encoding the mature chemokine β-15 polypeptide having the amino acid sequence encoded by the cDNA clone contained in ATCC Deposit No. 97519; and (f) a nucleotide sequence complementary to any of the nucleotide sequences in (a), (b), (c), (d), or (e) above. Preferably, the nucleic acid molecule will encode the mature polypeptide in SEQ ID NO:2 or encoded by the above-described deposited cDNA.

Further embodiments of the invention include isolated nucleic acid molecules that comprise a polynucleotide having a nucleotide sequence at least 90% identical, and more preferably at least 95%, 96%, 97%, 98% or 99% identical, to any of the nucleotide sequences in (a), (b), (c), (d), (e), or (f) above, or a polynucleotide which hybridizes under stringent hybridization conditions to a polynucleotide having a nucleotide sequence identical to a nucleotide sequence in (a), (b), (c), (d), (e), or (f), above. The polynucleotide which hybridizes does not hybridize under stringent hybridization conditions to a polynucleotide having a nucleotide sequence consisting of only A residues or of only T residues. An additional nucleic acid embodiment of the invention relates to an isolated nucleic acid molecule comprising a polynucleotide which encodes the amino acid sequence of an epitope-bearing portion of a chemokine β-5 polypeptide having an amino acid sequence in (a), (b), (c), (d), or (e), above.

The present invention also relates to recombinant vectors which include the isolated nucleic acid molecules of the present invention and to host cells containing the recombinant vectors, as well as to methods of making such vectors and host cells and for using them for production of CKβ-15 polypeptides or peptides by recombinant techniques.

The invention further provides an isolated chemokine β-15 polypeptide having amino acid sequence selected from the group consisting of: (a) a polypeptide comprising amino acids from about −20 to about 129 in SEQ ID NO:2; (b) a polypeptide comprising amino acids from about −19 to about 129 in SEQ ID NO:2; (c) a polypeptide comprising amino acids from about 1 to about 129 in SEQ ID NO:2; (d) the amino acid sequence of the chemokine β-15 polypeptide having the complete amino acid sequence including the leader encoded by the cDNA clone contained in ATCC Deposit No. 97519; and (e) the amino acid sequence of the mature chemokine β-15 polypeptide having the amino acid sequence encoded by the cDNA clone contained in ATCC Deposit No. 97519. The polypeptides of the present invention also include polypeptides having an amino acid sequence with at least 90% similarity, more preferably at least 95% similarity to those described in (a), (b), (c), (d), or (e) above, as well as polypeptides having an amino acid sequence at least 80% identical, more preferably at least 90% identical, and still more preferably 95%, 96%, 97%, 98% or 99% identical to those above.

An additional embodiment of this aspect of the invention relates to a peptide or polypeptide which has the amino acid sequence of an epitope-bearing portion of a chemokine β-15 polypeptide having an amino acid sequence described in (a), (b), (c), (d) or (e), above. Peptides or polypeptides having the amino acid sequence of an epitope-bearing portion of a chemokine β-15 polypeptide of the invention include portions of such polypeptides with at least six or seven, preferably at least nine, and more preferably at least about 30 amino acids to about 50 amino acids, although epitope-bearing polypeptides of any length up to and including the entire amino acid sequence of a polypeptide of the invention described above also are included in the invention. In another embodiment the invention provides an isolated antibody that binds specifically to a chemokine β-15 polypeptide having an amino acid sequence described in (a), (b), (c), (d) or (e) above.

The present inventors have discovered that CKβ-15 is expressed only in tissue of the thymus. FIG. 3. For a number of thymus disorders, significantly higher or lower levels of CKβ-15 gene expression can be detected in thymus tissue or bodily fluids (e.g., serum, plasma, urine, synovial fluid or spinal fluid) taken from an individual having such a disorder, relative to a "standard" CKβ-15 gene expression level, i.e., the CKβ-15 expression level in thymus tissue or bodily fluids from an individual not having the thymus disorder. Thus, the invention provides a diagnostic method useful during diagnosis of a thymus disorder, which involves (a) assaying chemokine β-15 gene expression level in cells or body fluid of that individual; (b) comparing that chemokine β-15 gene expression level with a standard chemokine β-15 gene expression level, whereby an increase or decrease in the assayed chemokine β-15 gene expression level compared to the standard expression level is indicative of a thymus disorder. An additional aspect of the invention is related to a method for treatment of an individual in need of an increased level of chemokine β-15 activity in the body comprising administering to such an individual a composition comprising an isolated chemokine β-15 polypeptide of the invention.

BRIEF DESCRIPTION OF THE DRAWINGS

FIGS. 1A–C show the nucleotide (SEQ ID NO:1) and deduced amino acid (SEQ ID NO:2) sequences of the complete chemokine β-15 protein determined by sequencing of the DNA clone contained in ATCC Deposit No. 97519. The protein has a leader sequence of about 20 amino acid residues (underlined) and a deduced molecular weight of about 16 kDa. The amino acid sequence of the predicted mature CKβ-15 protein is shown in FIGS. 1A–C (last 129 amino acids) and in SEQ ID NO:2 (from amino acid residue 1 to residue 129).

FIG. 2 shows the regions of similarity between the amino acid sequences of the CKβ-15 protein and the mouse macrophage inflammatory protein-related protein 2 (MMRP-2) [SEQ ID NO:3].

DETAILED DESCRIPTION OF THE INVENTION

Figure 3:
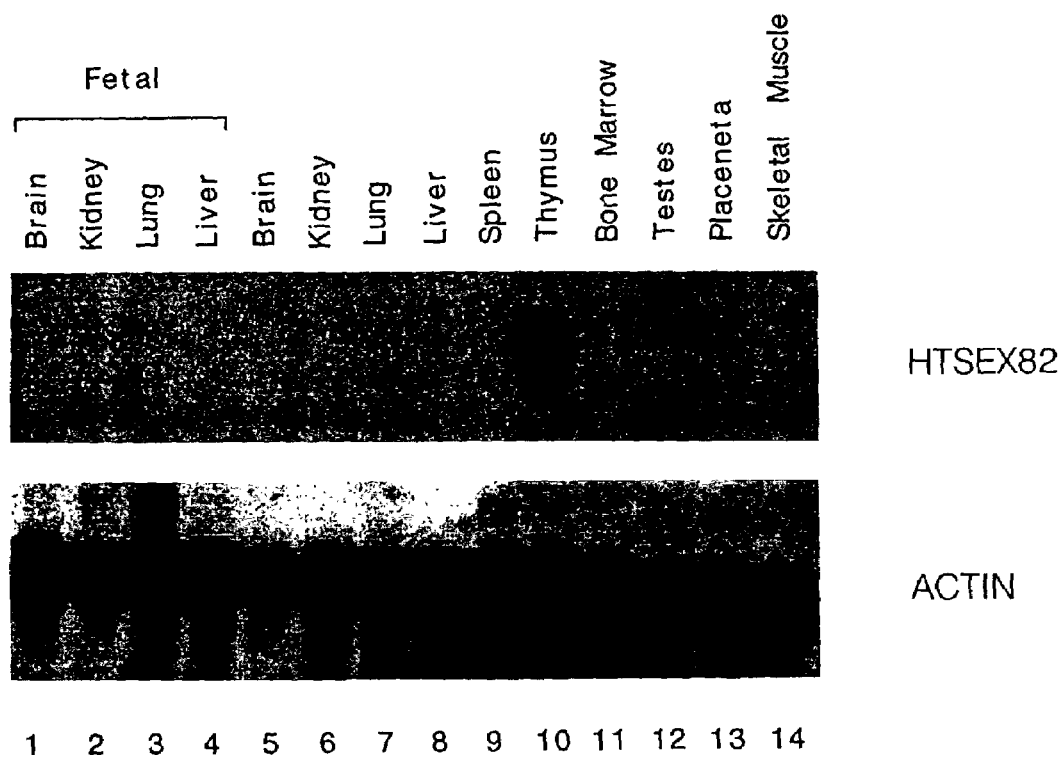
FIG. 3 shows a Northern blot assay for expression of mRNA from the CKβ-15 gene in various human tissues. The panel labeled "HTSEX82" shows hybridization to the CKβ-15 cDNA probe which that labeled "ACTIN" shows hybridization of a cDNA encoding actin which serves as a positive control indicating the presence of intact RNA in each sample.

The present invention provides isolated nucleic acid molecules comprising a polynucleotide encoding the chemokine β-15 (CKβ-15) protein having the amino acid sequence shown in FIGS. 1A–C (SEQ ID NO:2) which was determined by sequencing a cloned cDNA. CKβ-15 is a novel member of the β-chemokine subfamily (CC) whose genes are on human chromosome 17 and on mouse chromosome 11 (Wilson, S. D., et al., *J. Exp. Med.* 171.4301(1990) and Modi, W.S., et al., *Hum. Genet.* 84: 185 (1990)). The CKβ-15 protein of the present invention shares sequence homology with the mouse macrophage inflammatory protein-related protein 2 (MMRP-2) (FIG. 2) (SEQ ID NO:3). The nucleotide sequence shown in FIGS. 1A–C (SEQ ID NO:1) was obtained by sequencing the HTSEX82 cDNA clone encoding a CKβ-15 polypeptide, which was deposited on Apr. 25, 1996 at the American Type Culture Collection, Patent Depository, 10801 University Boulevard, Manassas, Va. 20110-2209. The deposited clone is contained in the Bluescript SK(−) plasmid (Stratagene, LaJolla, Calif.).

Nucleic Acid Molecules

Unless otherwise indicated, all nucleotide sequences determined by sequencing a DNA molecule herein were determined using an automated DNA sequencer (such as the Model 373 from Applied Biosystems, Inc.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain a some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Unless otherwise indicated, each "nucleotide sequence" set forth herein is presented as a sequence of deoxyribonucleotides (abbreviated A, G, C and T). However, by "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U) where each thymidine deoxynucleotide (T) in the specified deoxynucleotide sequence in is replaced by the ribonucleotide uridine (U). For instance, reference to an RNA molecule having the sequence of SEQ ID NO:1 set forth using deoxyribonucleotide abbreviations is intended to indicate an RNA molecule having a sequence in which each deoxynucleotide A, G or C of SEQ ID NO:1 has been replaced by the corresponding ribonucleotide A, G or C, and each deoxynucleotide T has been replaced by a ribonucleotide U.

Using the information provided herein, such as the nucleotide sequence in FIG. 1, a nucleic acid molecule of the present invention encoding a CKβ-15 polypeptide may be obtained using standard cloning and screening procedures, such as those for cloning cDNAs using mRNA as starting material. Illustrative of the invention, the nucleic acid molecule described in FIG. 1 [SEQ ID NO:1] was discovered in a cDNA library derived from human thymus tissue. The determined nucleotide sequence of the CKβ-15 cDNA of FIG. 1 contains an open reading frame encoding a protein of about 149 amino acid residues with an initiation codon at positions 1–3 of the nucleotide sequence shown in FIG. 1 [SEQ ID NO. 1], and a predicted leader sequence of about 20 amino acid residues, and a deduced molecular weight of about 16 kDa. The amino acid sequence of the predicted mature CKβ-15 protein is shown in FIG. 1 from amino acid residue 21 to residue 149 and in SEQ ID NO:2 from amino acid residue 1 to 129. The CKβ-15 protein shown in FIG. 1 [SEQ ID NO:2] is about 34% identical and about 53% similar to MMRP2 (FIG. 2).

The present invention also provides the mature form(s) of the CKβ-15 polypeptide of the present invention. According to the signal hypothesis, proteins secreted by mammalian cells have a signal or secretory leader sequence which is cleaved from the mature protein once export of the growing protein chain across the rough endoplasmic reticulum has been initiated. Most mammalian cells and even insect cells cleave secreted proteins with the same specificity. However, in some cases, cleavage of a secreted protein is not entirely uniform, which results in two or more mature species on the protein. Further, it has long been known that the cleavage specificity of a secreted protein is ultimately determined by the primary structure of the complete protein, that is, it is inherent in the amino acid sequence of the polypeptide. Therefore, the present invention provides a nucleotide sequence encoding the mature CKβ-5 polypeptides having the amino acid sequence encoded by the cDNA clone contained in the host identified as ATCC Deposit No. 97519 and as shown in SEQ ID NO:2. By the mature CKβ-15 protein having the amino acid sequence encoded by the cDNA clone contained in the host identified as ATCC Deposit No. 97519 is meant the mature form(s) of the CKβ-15 polypeptide produced by expression in a mammalian cell (e.g., COS cells, as described below) of the complete open reading frame encoded by the human DNA sequence of the clone contained in the vector in the deposited host. As indicated below, the mature CKβ-15 polypeptide having the amino acid sequence encoded by the cDNA clone contained in ATCC Deposit No. 97519 may or may not differ from the predicted "mature"CKβ-15 polypeptide shown in SEQ ID NO:2 (amino acids from about 1 to about 129) depending on the accuracy of the predicted cleavage site based on computer analysis.

Methods for predicting whether a protein has a secretory leader as well as the cleavage point for that leader sequence are available. For instance, the methods of McGeoch, Virus Res. 3, 271–286 (1985) and von Heinje, Nucleic Acids Res. 14, 4683–4690 (1986) can be used. The accuracy of predicting the cleavage points of known mammalian secretory proteins for each of these methods is in the range of 75–80%. von Heinje, supra. However, the two methods do not always produce the same predicted cleavage point(s) for a given protein.

In the present case, the predicted amino acid sequence of the complete CKβ-15 polypeptides of the present invention were analyzed by a computer program (PSORT) (Nakai, K. and Kanehisa, M. Genomics 14, 897–911 (1992)), which is an expert system for predicting the cellular location of a protein based on the amino acid sequence. As part of this computational prediction of localization, the methods of McGeoch and von Heinje are incorporated. The analysis by the PSORT program predicted the cleavage site between amino acids −1 and 1 in SEQ ID NO:2. Thereafter, the complete amino acid sequences were further analyzed by visual inspection, applying a simple form of the (−1,−3) rule of von Heinje. von Heinje, supra. Thus, the leader sequence for the CKβ-15 polypeptide is predicted to consist of amino acid residues from about −20 to about −1 in SEQ ID NO:2, while the mature CKβ-15 polypeptide is predicted to consist of residues from about 1 to about 129.

As one of ordinary skill would appreciate, due to the possibilities of sequencing errors discussed above, as well as the variability of cleavage sites for leaders in different known proteins, the actual CKβ-15 polypeptide encoded by the deposited cDNA comprises about 149 amino acids, but may be anywhere in the range of 142–154 amino acids; and the actual leader sequence of this protein is about 20 amino acids, but may be anywhere in the range of about 15 to about 25 amino acids.

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Isolated nucleic acid molecules of the present invention include DNA molecules comprising an open reading frame (ORF) with an initiation codon at positions 1–3 of the nucleotide sequence shown in FIG. 1 [SEQ ID NO:1]; DNA molecules comprising the coding sequence for the mature CKβ-15 protein shown in FIG. 1 (amino acid residues from about 21 to about 149) and SEQ ID NO:2 (amino acid residues from about 1 to about 129); and DNA molecules which comprise a sequence substantially different from those described above but which, due to the degeneracy of the genetic code, still encode the CKβ-15 protein. Of course, the genetic code is well known in the art. Thus, it would be routine for one skilled in the art to generate the degenerate variants described above.

In another aspect, the invention provides isolated nucleic acid molecules encoding the CKβ-15 polypeptide having an amino acid sequence encoded by the cDNA clone contained in the plasmid deposited as ATCC Deposit No. 97519 on Apr. 25, 1996. Preferably, this nucleic acid molecule will encode the mature polypeptide encoded by the above-described deposited cDNA clone. In a further embodiment, nucleic acid molecules are provided encoding the fill-length CKβ-15 polypeptide lacking the N-terminal methionine. The invention further provides an isolated nucleic acid molecule having the nucleotide sequence shown in FIG. 1 [SEQ ID NO:1] or the nucleotide sequence of the CKβ-15 cDNA contained in the above-described deposited clone, or nucleic acid molecule having a sequence complementary to one of the above sequences. Such isolated molecules, particularly DNA molecules, are useful as probes for gene mapping by in situ hybridization with chromosomes and for detecting expression of the CKβ-15 gene in human tissue, for instance, by Northern blot analysis. As described in detail below, detecting altered CKβ-15 gene expression in certain tissues or bodily fluids is indicative of thymus disorders.

The present invention is further directed to fragments of the isolated nucleic acid molecules described herein. By a fragment of an isolated nucleic acid molecule having the nucleotide sequence of the deposited cDNA or the nucleotide sequence shown in SEQ ID NO:1 is intended fragments at least about 15 nt, and more preferably at least about 20 nt, still more preferably at least about 30 nt, and even more preferably, at least about 40 nt in length which are useful as diagnostic probes and primers as discussed herein. Of course, larger fragments 50–500 nt in length are also useful according to the present invention as are fragments corresponding to most, if not all, of the nucleotide sequence of the deposited cDNA or as shown in SEQ ID NO:1. By a fragment at least 20 nt in length, for example, is intended fragments which include 20 or more contiguous bases from the nucleotide sequence of the deposited cDNA or the nucleotide sequence as shown in SEQ ID NO:1. Preferred nucleic acid fragments of the present invention include nucleic acid molecules encoding epitope-bearing portions of the CKβ-15 protein.

In another aspect, the invention provides an isolated nucleic acid molecule comprising a polynucleotide which hybridizes under stringent hybridization conditions to a portion of the polynucleotide in a nucleic acid molecule of the invention described above, for instance, the cDNA clone contained in ATCC Deposit 97519. By "stringent hybridization conditions" is intended overnight incubation at 42° C. in a solution comprising: 50% formamide, 5×SSC (750 mM NaCl, 75mM trisodium citrate), 50 mM sodium phosphate (pH7.6), 5 × Denhardt's solution, 10% dextran sulfate, and 20 µg/ml denatured, sheared salmon sperm DNA, followed by washing the filters in 0.1×SSC at about 65° C. By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 nt of the reference polynucleotide. These are useful as diagnostic probes and primers as discussed above and in more detail below.

Of course, polynucleotides hybridizing to a larger portion of the reference polynucleotide (e.g., the deposited cDNA clone), for instance, a portion 50–750 nt in length, or even to the entire length of the reference polynucleotide, also useful as probes according to the present invention, as are polynucleotides corresponding to most, if not all, of the nucleotide sequence of the deposited cDNA or the nucleotide sequence as shown in FIG. 1 [SEQ ID NO:1]. By a portion of a polynucleotide of "at least 20 nt in length," for example, is intended 20 or more contiguous nucleotides from the nucleotide sequence of the reference polynucleotide, (e.g., the deposited cDNA or the nucleotide sequence as shown in FIG. 1 [SEQ ID NO:1]). As indicated, such portions are useful diagnostically either as a probe according to conventional DNA hybridization techniques or as primers for amplification of a target sequence by the polymerase chain reaction (PCR), as described, for instance, in *Molecular Cloning, A Laboratory Manual,* 2nd. edition, edited by Sambrook, J., Fritsch, E. F. and Maniatis, T., (1989), Cold Spring Harbor Laboratory Press, the entire disclosure of which is hereby incorporated herein by reference.

Since a CKβ-15 cDNA clone has been deposited and its determined nucleotide sequence is provided in FIG. 1 [SEQ ID NO:1], generating polynucleotides which hybridize to a portion of the CKβ-15 cDNA molecule would be routine to the skilled artisan. For example, restriction endonuclease cleavage or shearing by sonication of the CKβ-15 cDNA clone could easily be used to generate DNA portions of various sizes which are polynucleotides that hybridize to a portion of the CKβ-15 cDNA molecule. Alternatively, the hybridizing polynucleotides of the present invention could be generated synthetically according to known techniques. Of course, a polynucleotide which hybridizes only to a poly A sequence (such as the 3' terminal poly(A) tract of the CKβ-15 cDNA shown in FIG. 1 [SEQ ID NO:1]), or to a complementary stretch of T (or U) resides, would not be included in a polynucleotide of the invention used to hybridize to a portion of a nucleic acid of the invention, since such a polynucleotide would hybridize to any nucleic acid molecule contain a poly (A) stretch or the complement thereof (e.g., practically any double-stranded cDNA clone).

As indicated, nucleic acid molecules of the present invention which encode the CKβ-15 protein polypeptide may include, but are not limited to those encoding the amino acid sequence of the mature polypeptide, by itself; the coding sequence for the mature polypeptide and additional sequences, such as those encoding the about 20 amino acid leader or secretory sequence, such as a pre-, or pro- or prepro-protein sequence; the coding sequence of the mature polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing—including splicing and polyadenylation signals, for example—ribosome binding and stability of mRNA; an additional coding sequence which codes for additional amino acids, such as those which provide additional functionalities. Thus, the sequence encoding the polypeptide may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (Qiagen, Inc.), among others, many of which are commercially available. As described in Gentz et al. (1989) Proc. Natl. Acad. Sci., USA 86:821–824, for instance, hexa-histidine provides for convenient purification of the fusion protein. The "HA" tag is another peptide useful for purification which corresponds to an epitope derived from the influenza hemagglutinin protein, which has been described by Wilson et al., Cell 37: 767 (1984). As discussed below, other such fusion proteins include the CKβ-15 polypeptide fused to Fc at the N- or C-terminus.

The present invention further relates to variants of the nucleic acid molecules of the present invention, which encode portions, analogs or derivatives of the CKβ-15 protein. Variants may occur naturally, such as a natural allelic variant. By an "allelic variant" is intended one of several alternate forms of a gene occupying a given locus on a chromosome of an organism. Genes II, Lewin, ed. Non-naturally occurring variants may be produced using art-known mutagenesis techniques.

Such variants include those produced by nucleotide substitutions, deletions or additions. The substitutions, deletions or additions may involve one or more nucleotides. The variants may be altered in coding or non-coding regions or both. Alterations in the coding regions may produce conservative or non-conservative amino acid substitutions, deletions or additions. Especially preferred among these are silent substitutions, additions and deletions, which do not alter the properties and activities of the CKβ-15 protein or portions thereof. Also especially preferred in this regard are conservative substitutions. Most highly preferred are nucleic acid molecules encoding the mature CKβ-15 protein having the amino acid sequence shown in FIG. 1 [SEQ ID NO:2] or the mature CKβ-15 amino acid sequence encoded by the deposited cDNA clone.

Further embodiments of the invention include isolated nucleic acid molecules comprising a polynucleotide having a nucleotide sequence at least 90% identical, and more preferably at least 95%, 96%, 97%, 98% or 99% identical to (a) a nucleotide sequence encoding the chemokine β-15 polypeptide having the complete amino acid sequence in SEQ ID NO:2; (b) a nucleotide sequence encoding the chemokine β-15 polypeptide having the complete amino acid sequence in SEQ ID NO:2 but lacking the N-terminal methionine residue; (c) a nucleotide sequence encoding the mature chemokine β-15 polypeptide having the amino acid sequence at positions from about 1 to about 129 in SEQ ID NO:2; (d) a nucleotide sequence encoding the chemokine β-15 polypeptide having the complete amino acid sequence encoded by the cDNA clone contained in ATCC Deposit No. 97519; (e) a nucleotide sequence encoding the mature chemokine β-15 polypeptide having the amino acid sequence encoded by the cDNA clone contained in ATCC Deposit No. 97519; and (f) a nucleotide sequence complementary to any of the nucleotide sequences in (a), (b), (c), (d), or (e) above.

By a polynucleotide having a nucleotide sequence at least, for example, 95% "identical" to a reference nucleotide sequence encoding a chemokine β-15 polypeptide is intended that the nucleotide sequence of the polynucleotide is identical to the reference sequence except that the polynucleotide sequence may include up to five point mutations per each 100 nucleotides of the reference nucleotide sequence encoding the chemokine β-15 polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 90%, 95%, 96%, 97%, 98% or 99% identical to, for instance, the nucleotide sequence shown in FIG. 1 or to the nucleotides sequence of the deposited cDNA clone can be determined conventionally using known computer programs such as the Bestfit program (Wisconsin Sequence Analysis Package, Version 8 for Unix, Genetics Computer Group, University Research Park, 575 Science Drive, Madison, Wis. 53711. Bestfit uses the local homology algorithm of Smith and Waterman (Advances in Applied Mathematics 2: 482–489, 1981) to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

The present application is directed to nucleic acid molecules at least 90%, 95%, 96%, 97%, 98% or 99% identical to the nucleic acid sequence shown in FIG. 1 [SEQ ID NO:1] or to the nucleic acid sequence of the deposited cDNA, irrespective of whether they encode a polypeptide having CKβ-15 activity. This is because, even where a particular nucleic acid molecule does not encode a polypeptide having CKβ-15 activity, one of skill in the art would still know how to use the nucleic acid molecule, for instance, as a hybridization probe or a polymerase chain reaction (PCR) primer. Uses of the nucleic acid molecules of the present invention that do not encode a polypeptide having CKβ-15 activity include, inter alia, (1) isolating the CKβ-15 gene or allelic variants thereof in a cDNA library; (2) in situ hybridization (e.g., "FISH") to metaphase chromosomal spreads to provide precise chromosomal location of the CKβ-15 gene as described in Verma et al., *Human Chromosomes: a Manual of Basic Techniques,* Pergamon Press, New York (1988); and Northern Blot analysis for detecting CKβ-15 mRNA expression in specific tissues (e.g., thymus tissue).

Preferred, however, are nucleic acid molecules having sequences at least 90%, 95%, 96%, 97%, 98% or 99% identical to the nucleic acid sequence shown in FIG. 1 [SEQ ID NO:1] or to the nucleic acid sequence of the deposited cDNA which do, in fact, encode a polypeptide having CKβ-15 protein activity. By "a polypeptide having CKβ-15 activity" is intended polypeptides exhibiting activity similar, but not necessarily identical, to an activity of the CKβ-15 protein of the invention (either the full-length protein or, preferably, the mature protein) as measured in a particular biological assay. Like other CC cytokines, CKβ-15 exhibits activity on monocytes, lymphocytes and neutrophils. However, unlike other known CC cytokines, CKβ-15 has been shown to be expressed only in the thymus. Therefore, CKβ-15 is particularly active in modulating activities of cells in the thymus, particularly early thymocytes. For example, stimulation of early thymocyte proliferation by CKβ-15 is assayed in a standard proliferation assay (see, for instance, Spits et al. (1987) J. Immunol. 139:1142; Dalloul et al. (1989) Eur. J. Immunol. 19:1985; Murphy et al., (1992) Ped. Res. 32:269; Ruggiero et al, (1996) J. Immunol. 156: 3737). Briefly, the assay involves purification of thymocytes from human thymus, plating them in media with or without CKβ-15, and determining the change with elapsed time in the rate of proliferation or the number of cells compared to control cultures, by conventional means. Representative cell lines could also be employed in such assays.

CKβ-15 also mediates the differentiation of intrathymic T cell precursors into mature T-lymphocytes which are either α/β+ or γ/δ+ T cell receptor lymphocytes (as defined in Barcena et al. (1990) J. Exp. Med. 172:439). This effect is mediated by modulating (either inducing or inhibiting) the apoptosis of specific subsets of thymocytes within the thymus or by directly inducing the differentiation of a specific subset. In addition CKβ-15 also directs the homing of the immature lymphocyte precursor to the thymus for proper maturation. This activity is demonstrated by in vitro chemotaxis assays using primary progenitors or representative cell lines. CKβ-15 also mediates proper T-lymphocyte maturation via the thymic epithelial cells, for example, by providing a co-stimulatory signal for proliferation or differentiation, as shown by various in vitro assays for human thymocyte proliferation or differentiation (Ruggiero et al. (1996) J. Immunol. 156:3737; Barcena et al. (1990) J. Exp. Med. 172:439; Singer et al. (1990) J. Immunol. 144:2931).

The CKβ-15 protein of the present invention also modulates colony formation of bone marrow progenitor cells, as does the macrophage inflammatory protein related protein-2 (MMRP-2). An in vitro colony forming assay for measuring the extent of inhibition of myeloid progenitor cells is described in Youn et al., *The Journal of Immunology* 155: 2661–2667 (1995). Briefly, the assay involves collecting human or mouse bone marrow cells and plating the same on agar, adding one or more growth factors and either (1) transfected host cell-supernatant containing CKβ-15 protein (or a candidate polypeptide) or (2) nontransfected host cell-supernatant control, and measuring the effect on colony formation by murine and human CFU-granulocyte-macrophages (CFU-GM), by human burst-forming unit-erythroid (BFU-E), or by human CFU granulocyte-erythroid-macrophage-megakaryocyte (CFU-GEMM).

CKβ-15 protein modulates early thymocyte proliferation and differentiation in a dose-dependent manner in the above-described assays. Thus, "a polypeptide having CKβ-15 protein activity" includes polypeptides that also exhibit any of the same thymocyte modulating activities in the above-described assays in a dose-dependent manner. Although the degree of dose-dependent activity need not be identical to that of the CKβ-15 protein, preferably, "a polypeptide having CKβ-15 protein activity" will exhibit substantially similar dose-dependence in a given activity as compared to the CKβ-15 protein (i.e., the candidate polypeptide will exhibit greater activity or not more than about tenfold less and, preferably, not more than about twofold less activity relative to the reference CKβ-15 protein).

Of course, due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequence of the deposited cDNA or the nucleic acid sequence shown in FIG. 1 [SEQ ID NO:1] will encode a polypeptide "having CKβ-15 protein activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having CKβ-15 protein activity. This is because the skilled artisan is fully aware of amino acid substitutions that are either less likely or not likely to significantly effect protein function (e.g., replacing one aliphatic amino acid with a second aliphatic amino acid).

For example, guidance concerning how to make phenotypically silent amino acid substitutions is provided in Bowie, J. U., et al., "Deciphering the Message in Protein Sequences: Tolerance to Amino Acid Substitutions," *Science* 247:1306–1310 (1990), wherein the authors indicate that there are two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selections or screens to identify sequences that maintain functionality. As the authors state, these studies have revealed that proteins are surprisingly tolerant of amino acid substitutions. The authors further indicate which amino acid changes are likely to be permissive at a certain position of the protein. For example, most buried amino acid residues require nonpolar side chains, whereas few features of surface side chains are generally conserved. Other such phenotypically silent substitutions are described in Bowie, J. U., et al., supra, and the references cited therein.

Vectors and Host Cells

The present invention also relates to vectors which include the isolated DNA molecules of the present invention, host cells which are genetically engineered with the recombinant vectors, and the production of CKβ-15 polypeptides or portions thereof by recombinant techniques.

Recombinant constructs may be introduced into host cells using well known techniques such as infection, transduction, transfection, transvection, electroporation and transformation. The vector may be, for example, a phage, plasmid, viral or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

Preferred are vectors comprising cis-acting control regions to the polynucleotide of interest. Appropriate transacting factors may be supplied by the host, supplied by a complementing vector or supplied by the vector itself upon introduction into the host.

In certain preferred embodiments in this regard, the vectors provide for specific expression, which may be inducible and/or cell type-specific. Particularly preferred among such vectors are those inducible by environmental factors that are easy to manipulate, such as temperature and nutrient additives.

Expression vectors useful in the present invention include chromosomal-, episomal- and virus-derived vectors, e.g., vectors derived from bacterial plasmids, bacteriophage, yeast episomes, yeast chromosomal elements, viruses such as baculoviruses, papova viruses, vaccinia viruses, adenoviruses, fowl pox viruses, pseudorabies viruses and retroviruses, and vectors derived from combinations thereof, such as cosmids and phagemids.

The DNA insert should be operatively linked to an appropriate promoter, such as the phage lambda PL promoter, the E. coli lac, trp and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs will include a translation initiating AUG at the beginning and a termination codon appropriately positioned at the end of the polypeptide to be translated.

As indicated, the expression vectors will preferably include at least one selectable marker. Such markers include dihydrofolate reductase or neomycin resistance for eukaryotic cell culture and tetracycline or ampicillin resistance genes for culturing in E. coli and other bacteria. Representative examples of appropriate hosts include bacterial cells, such as E. coli, Streptomyces and Salmonella typhimurium cells; fungal cells, such as yeast cells; insect cells such as Drosophila S2 and Spodoptera Sf9 cells; animal cells such as CHO, COS and Bowes melanoma cells; and plant cells. Appropriate culture media and conditions for the above-described host cells are known in the art.

Among vectors preferred for use in bacteria include pA2, pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia Other suitable vectors will be readily apparent to the skilled artisan.

Among known bacterial promoters suitable for use in the present invention include the E. coli lacI and lacZ promoters, the T3 and T7 promoters, the gpt promoter, the lambda PR and PL promoters and the trp promoter. Suitable eukaryotic promoters include the CMV immediate early promoter, the HSV thymidine kinase promoter, the early and late SV40 promoters, the promoters of retroviral LTRs, such as those of the Rous sarcoma virus (RSV), and metallothionein promoters, such as the mouse metallothionein-I promoter.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., BASIC METHODS IN MOLECULAR BIOLOGY, (1986).

Transcription of the DNA encoding the polypeptides of the present invention by higher eukaryotes may be increased by inserting an enhancer sequence into the vector. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at bp 100 to 270, the cytomegalovirus early promoter enhancer, the polyoma enhancer on the late side of the replication origin, and adenovirus enhancers.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous signals.

The polypeptide may be expressed in a modified form, such as a fusion protein, and may include not only secretion signals, but also additional heterologous functional regions. Thus, for instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize proteins. For example, EPA 0 464 533 (Canadian counterpart 2045869) discloses fusion proteins comprising various portions of constant region of immunoglobin molecules together with another human protein or part thereof. In many cases, the Fe part in a fusion protein is thoroughly advantageous for use in therapy and diagnosis and thus results, for example, in improved pharmacokinetic properties (EPA 0 232 262). On the other hand, for some uses it would be desirable to be able to delete the Fc part after the fusion protein has been expressed, detected and purified in the advantageous manner described. This is the case when the Fc portion proves to be a hindrance to use in therapy and diagnosis, for example when the fusion protein is to be used as an antigen for immunizations. In drug discovery, for example, human proteins, such as the hIL5-receptor, have been fused with Fc portions for the purpose of high-throughput screening assays to identify antagonists of hIL-5. See, D. Bennett et al., *J. of Molec. Recognition* 8:52–58 (1995) and K. Johanson et al., *J. Biol. Chem.* 270:9459–9471 (1995).

The CKβ-15 protein can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

CKβ-15 Polypeptides and Peptides

The invention further provides an isolated CKβ-15 polypeptide having the amino acid sequence encoded by the deposited cDNA, or the amino acid sequence in FIG. 1 [SEQ ID NO:2], or a peptide or polypeptide comprising a portion of the above polypeptides. The terms "peptide" and "oligopeptide" are considered synonymous (as is commonly recognized) and each term can be used interchangeably as the context requires to indicate a chain of at least ten amino acids coupled by peptidyl linkages. The word "polypeptide" is used herein for chains containing more than ten amino acid residues. All oligopeptide and polypeptide formulas or sequences herein are written from left to right and in the direction from amino terminus to carboxy terminus.

It will be recognized in the art that some amino acid sequence of the CKβ-15 polypeptide can be varied without significant effect of the structure or function of the protein. If such differences in sequence are contemplated, it should be remembered that there will be critical areas on the protein which determine activity. In general, it is possible to replace residues which form the tertiary structure, provided that residues performing a similar function are used. In other instances, the type of residue may be completely unimportant if the alteration occurs at a non-critical region of the protein.

Thus, the invention further includes variations of the CKβ-15 polypeptide which show substantial CKβ-15 polypeptide activity or which include regions of CKβ-15 protein such as the protein portions discussed below. Such mutants include deletions, insertions, inversions, repeats, and type substitutions (for example, substituting one hydrophilic residue for another, but not strongly hydrophilic for strongly hydrophobic as a rule). Small changes or such "neutral" amino acid substitutions will generally have little effect on activity.

Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

As indicated in detail above, further guidance concerning which amino acid changes are likely to be phenotypically silent (i.e., are not likely to have a significant deleterious effect on a function) can be found in Bowie, J. U., et al., "Deciphering the Message in Protein Sequences: Tolerance to Amino Acid Substitutions," *Science* 247:1306–1310 (1990).

Thus, the fragment, derivative or analog of the polypeptide of SEQ ID NO:2, or that encoded by the deposited cDNA, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as an IgG Fc fusion region peptide or leader or secretory sequence or a sequence which is employed for purification of the mature polypeptide or a proprotein sequence. Such fragments, derivatives and analogs are deemed to be within the scope of those skilled in the art from the teachings herein.

Of particular interest are substitutions of charged amino acids with another charged amino acid and with neutral or negatively charged amino acids. The latter results in proteins with reduced positive charge to improve the characteristics of the CKβ-15 protein. The prevention of aggregation is highly desirable. Aggregation of proteins not only results in a loss of activity but can also be problematic when preparing pharmaceutical formulations, because they can be immunogenic. (Pinckard et al., *Clin Exp. Immunol.* 2:331–340 (1967); Robbins et al., *Diabetes* 36:838–845 (1987); Cleland et al., *Crit. Rev. Therapeutic Drug Carrier Systems* 10:307–377 (1993)).

As indicated, changes are preferably of a minor nature, such as conservative amino acid substitutions that do not significantly affect the folding or activity of the protein (see Table 1).

TABLE 1

Conservative Amino Acid Substitutions.

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Amino acids in the CKβ-15 protein of the present invention that are essential for function can be identified by methods known in the art, such as site-directed mutagenesis or alamine-scanning mutagenesis (Cunningham and Wells, Science 244:1081–1085 (1989)). The latter procedure introduces single alanine mutations at every residue in the molecule. The resulting mutant molecules are then tested for biological activity. Sites that are critical for ligand-receptor binding can also be determined by structural analysis such as crystallization, nuclear magnetic resonance or photoaffinity labeling (Smith et al., J. Mol. Biol. 224:899–904 (1992) and de Vos et al. Science 255:306–312 (1992)).

The polypeptides of the present invention are preferably provided in an isolated form. By "isolated polypeptide" is intended a polypeptide removed from its native environment. Thus, a polypeptide produced and/or contained within a recombinant host cell is considered isolated for purposes of the present invention. Also intended as an "isolated polypeptide" are polypeptides that have been purified, partially or substantially, from a recombinant host cell. For example, a recombinantly produced version of the CKβ-15 polypeptide can be substantially purified by the one-step method described in Smith and Johnson, Gene 67:3140 (1988).

The polypeptides of the present invention include the polypeptide encoded by the deposited cDNA including the leader; the mature polypeptide encoded by the deposited cDNA minus the leader (i.e., the mature protein); a polypeptide comprising amino acids from about –20 to about 129 in SEQ ID NO:2; a polypeptide comprising amino acids from about –19 to about 129 in SEQ ID NO:2; a polypeptide comprising amino acids from about 1 to about 129 in SEQ ID NO:2; as well as polypeptides which are at least 80% identical, more preferably at least 90% or 95% identical, still more preferably at least 96%, 97%, 98% or 99% identical to the polypeptides described above and also include portions of such polypeptides with at least 30 amino acids and more preferably at least 50 amino acids.

By "% similarity" for two polypeptides is intended a similarity score produced by comparing the amino acid sequences of the two polypeptides using the Bestfit program (Wisconsin Sequence Analysis Package, Version 8 for Unix, Genetics Computer Group, University Research Park, 575 Science Drive, Madison, Wis. 53711) and the default settings for determining similarity. Bestfit uses the local homology algorithm of Smith and Waterman (Advances in Applied Mathematics 2: 482–489, 1981) to find the best segment of similarity between two sequences.

By a polypeptide having an amino acid sequence at least, for example, 95% "identical" to a reference amino acid sequence of a chemokine β-15 polypeptide is intended that the amino acid sequence of the polypeptide is identical to the reference sequence except that the polypeptide sequence may include up to five amino acid alterations per each 100 amino acids of the reference amino acid of the chemokine β-15 polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequence shown in FIG. 1 [SEQ ID NO:2] or to the amino acid sequence encoded by deposited cDNA clone can be determined conventionally using known computer programs such the Bestfit program (Wisconsin Sequence Analysis Package, Version 8 for Unix, Genetics Computer Group, University Research Park, 575 Science Drive, Madison, Wis. 53711. When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

The polypeptide of the present invention are useful as a molecular weight marker on SDS-PAGE gels or on molecular sieve gel filtration columns using methods well known to those of skill in the art.

As described in detail below, the polypeptides of the present invention can be used to raise polyclonal and monoclonal antibodies, which are useful in diagnostic assays for detecting CKβ-15 protein expression as described below or as agonists and antagonists capable of enhancing or inhibiting CKβ-15 protein function. Further, such polypeptides can be used in the yeast two-hybrid system to "capture" CKβ-15 protein binding proteins which are also candidate agonist and antagonist according to the present invention. The yeast two hybrid system is described in Fields and Song, Nature 340:245–246 (1989).

In another aspect, the invention provides a peptide or polypeptide comprising an epitope-bearing portion of a polypeptide of the invention. The epitope of this polypeptide portion is an immunogenic or antigenic epitope of a polypeptide of the invention. An "immunogenic epitope" is defined as a part of a protein that elicits an antibody response when the whole protein is the immunogen. These immunogenic epitopes are believed to be confined to a few loci on the molecule. On the other hand, a region of a protein molecule to which an antibody can bind is defined as an "antigenic epitope." The number of immunogenic epitopes of a protein generally is less than the number of antigenic epitopes. See, for instance, Geysen, H. M., Meloen, R. H. and Barteling, S. J. (1984) Use of peptide synthesis to probe viral antigens for epitopes to a resolution of a single amino acid. Proc. Natl. Acad. Sci. USA 81:3998–4002.

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G., Shinnick, T. M., Green, N. and Learner, R. A. (1983) Antibodies that react with predetermined sites on proteins. Science 219:660–666. Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Peptides that are extremely hydrophobic and those of six or fewer residues generally are ineffective at inducing antibodies that bind to the mimicked protein; longer, soluble peptides, especially those containing proline residues, usually are effective. Sutcliffe et al., supra, at 661. For instance, 18 of 20 peptides designed according to these guidelines, containing 8–39 residues covering 75% of the sequence of the influenza virus hemagglutinin HA1 polypeptide chain, induced antibodies that reacted with the HA1 protein or intact virus; and 12/12 peptides from the MuLV polymerase and 18/18 from the rabies glycoprotein induced antibodies that precipitated the respective proteins.

Antigenic epitope-bearing peptides and polypeptides of the invention are therefore useful to raise antibodies, including monoclonal antibodies, that bind specifically to a polypeptide of the invention. Thus, a high proportion of hybridomas obtained by fusion of spleen cells from donors immunized with an antigen epitope-bearing peptide generally secrete antibody reactive with the native protein. Sutcliffe et al., supra, at 663. The antibodies raised by antigenic epitope-bearing peptides or polypeptides are useful to detect the mimicked protein, and antibodies to different peptides may be used for tracking the fate of various regions of a protein precursor which undergoes posttranslation processing. The peptides and anti-peptide antibodies may be used in a variety of qualitative or quantitative assays for the mimicked protein, for instance in competition assays since it has been shown that even short peptides (e.g., about 9 amino acids) can bind and displace the larger peptides in immunoprecipitation assays. See, for instance, Wilson, I. A., Niman, H. L., Houghten, R. A., Cherenson, A. R., Connolly, M. L. and Lerner, R. A. (1984) The structure of an antigenic determinant in a protein. Cell 37:767–778 at 777. The anti-peptide antibodies of the invention also are useful for purification of the mimicked protein, for instance, by adsorption chromatography using methods well known in the art.

Antigenic epitope-bearing peptides and polypeptides of the invention designed according to the above guidelines preferably contain a sequence of at least seven, more preferably at least nine and most preferably between about 15 to about 30 amino acids contained within the amino acid sequence of a polypeptide of the invention. However, peptides or polypeptides comprising a larger portion of an amino acid sequence of a polypeptide of the invention, containing about 30 to about 50 amino acids, or any length up to and including the entire amino acid sequence of a polypeptide of the invention, also are considered epitope-bearing peptides or polypeptides of the invention and also are useful for inducing antibodies that react with the mimicked protein. Preferably, the amino acid sequence of the epitope-bearing peptide is selected to provide substantial solubility in aqueous solvents (i.e., the sequence includes relatively hydrophilic residues and highly hydrophobic sequences are preferably avoided); and sequences containing proline residues are particularly preferred.

The epitope-bearing peptides and polypeptides of the invention may be produced by any conventional means for making peptides or polypeptides including recombinant means using nucleic acid molecules of the invention. For instance, a short epitope-bearing amino acid sequence may be fused to a larger polypeptide which acts as a carrier during recombinant production and purification, as well as during immunization to produce anti-peptide antibodies. Epitope-bearing peptides also may be synthesized using known methods of chemical synthesis. For instance, Houghten has described a simple method for synthesis of large numbers of peptides, such as 10–20 mg of 248 different 13 residue peptides representing single amino acid variants of a segment of the HA1 polypeptide which were prepared and characterized (by ELISA-type binding studies) in less than four weeks. Houghten, R. A. (1985) General method for the rapid solid-phase synthesis of large numbers of peptides: specificity of antigen-antibody interaction at the level of individual amino acids. Proc. Natl. Acad. Sci. USA 82:5131–5135. This "Simultaneous Multiple Peptide Synthesis (SMPS)" process is further described in U.S. Pat. No. 4,631,211 to Houghten et al. (1986). In this procedure the individual resins for the solid-phase synthesis of various peptides are contained in separate solvent-permeable packets, enabling the optimal use of the many identical repetitive steps involved in solid-phase methods. A completely manual procedure allows 500–1000 or more syntheses to be conducted simultaneously. Houghten et al., supra, at 5134.

Epitope-bearing peptides and polypeptides of the invention are used to induce antibodies according to methods well known in the art See, for instance, Sutcliffe et al., supra; Wilson et al., supra; Chow, M., Yabrov, R., Bittle, J., Hogel, J. and Baltimore, D., Proc. Natl. Acad. Sci. USA 82:910–914; and Bittle, F. J., Fry, C. M., Rowlands, D. J., Brown, F., Bittle, J. L., Houghten, R. A. and Lerner, R. A. (1985) J. Gen. Virol. 66:2347–2354. Generally, animals may be immunized with free peptide; however, anti-peptide antibody titer may be boosted by coupling of the peptide to a macromolecular carrier, such as keyhole limpet hemacyanin (KLH) or tetanus toxoid. For instance, peptides containing cysteine may be coupled to carrier using a linker such as m-maleimidobenzoyl-N-hydroxysuccinimide ester (MBS), while other peptides may be coupled to carrier using a more general linking agent such as glutaraldehyde. Animals such as rabbits, rats and mice are immunized with either free or carrier-coupled peptides, for instance, by intraperitoneal and/or intradermal injection of emulsions containing about 100 μg peptide or carrier protein and Freund's adjuvant. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

Immunogenic epitope-bearing peptides of the invention, i.e., those parts of a protein that elicit an antibody response when the whole protein is the immunogen, are identified according to methods known in the art. For instance, Geysen et al., 1984, supra, discloses a procedure for rapid concurrent synthesis on solid supports of hundreds of peptides of sufficient purity to react in an enzyme-linked immunosorbent assay. Interaction of synthesized peptides with antibodies is then easily detected without removing them from the support. In this manner a peptide bearing an immunogenic epitope of a desired protein may be identified routinely by one of ordinary skill in the art. For instance, the immunologically important epitope in the coat protein of foot-and-mouth disease virus was located by Geysen et al. with a resolution of seven amino acids by synthesis of an overlapping set of all 208 possible hexapeptides covering the entire 213 amino acid sequence of the protein. Then, a complete replacement set of peptides in which all 20 amino acids were substituted in turn at every position within the epitope were synthesized, and the particular amino acids conferring specificity for the reaction with antibody were determined. Thus, peptide analogs of the epitope-bearing peptides of the invention can be made routinely by this method. U.S. Pat. No.

4,708,781 to Geysen (1987) further describes this method of identifying a peptide bearing an immunogenic epitope of a desired protein.

Further still, U.S. Pat. No. 5,194,392 to Geysen (1990) describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, U.S. Pat. No. 4,433,092 to Geysen (1989) describes a method of detecting or determining a sequence of monomers which is a topographical equivalent of a ligand which is complementary to the ligand binding site of a particular receptor of interest. Similarly, U.S. Pat. No. 5,480,971 to Houghten, R. A. et al. (1996) on Peralkylated Oligopeptide Mixtures discloses linear $C_1$–$C_7$-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

The entire disclosure of each document cited in this section on "Polypeptides and Peptides" is hereby incorporated herein by reference.

Thymus-Related Disorder Diagnosis

The present inventors have discovered that CKβ-15 is expressed only in thymus tissue. For a number of thymus-related disorders, substantially altered (increased or decreased) levels of CKβ-15 gene expression can be detected in thymus tissue or other cells or bodily fluids (e.g., sera, plasma, urine, synovial fluid or spinal fluid) taken from an individual having such a disorder, relative to a "standard" CKβ-15 gene expression level, that is, the CKβ-15 expression level in thymus tissue or bodily fluids from an individual not having the thymus disorder. Thus, the invention provides a diagnostic method useful during diagnosis of a thymus disorder, which involves measuring the expression level of the gene encoding the CKβ-15 protein in thymus tissue or other cells or body fluid from an individual and comparing the measured gene expression level with a standard CKβ-15 gene expression level, whereby an increase or decrease in the gene expression level compared to the standard is indicative of a thymus disorder.

By individual is intended mammalian individuals, preferably humans. By "measuring the expression level of the gene encoding the CKβ-15 protein" is intended qualitatively or quantitatively measuring or estimating the level of the CKβ-15 protein or the level of the mRNA encoding the CKβ-15 protein in a first biological sample either directly (e.g., by determining or estimating absolute protein level or mRNA level) or relatively (e.g., by comparing to the CKβ-15 protein level or mRNA level in a second biological sample). Preferably, the CKβ-15 protein level or mRNA level in the first biological sample is measured or estimated and compared to a standard CKβ-15 protein level or mRNA level, the standard being taken from a second biological sample obtained from an individual not having the disorder or being determined by averaging levels from a population of individuals not having a disorder of the thymus. As will be appreciated in the art, once a standard CKβ-15 protein level or mRNA level is known, it can be used repeatedly as a standard for comparison.

By "biological sample" is intended any biological sample obtained from an individual, body fluid, cell line, tissue culture, or other source which contains CKβ-15 protein or mRNA. As indicated, biological samples include body fluids (such as sera, plasma, urine, synovial fluid and spinal fluid) which contain secreted mature CKβ-15 protein, thymus tissue, and other tissue sources found to express CKβ-15 or a CKβ-15 receptor. Methods for obtaining tissue biopsies and body fluids from mammals are well known in the art. Where the biological sample is to include mRNA, a tissue biopsy is the preferred source.

The present invention is useful for diagnosis or treatment of various thymus-related disorders in mammals, preferably humans. Such disorders include the following tumors and cancers, hypoactivity, hyperactivity, atrophy, enlargement of the thymus, and the like. Other disorders include disregulation of T-lymphocyte selection or activity and would include but not be limited to disorders involving autoimmunity, arthritis, leukemias, lymphomas, immunosuppression, sepsis, would healing, acute and chronic inflammation, cell mediated immunity, humor immunity, TH1/TH2 imbalance, and the like.

Total cellular RNA can be isolated from a biological sample using any suitable technique such as the single-step guanidinium-thiocyanate-phenol-chloroform method described in Chomczynski and Sacchi, *Anal. Biochem.* 162: 156–159 (1987). Levels of mRNA encoding the CKβ-15 protein are then assayed using any appropriate method. These include Northern blot analysis, S1 nuclease mapping, the polymerase chain reaction (PCR), reverse transcription in combination with the polymerase chain reaction (RT-PCR), and reverse transcription in combination with the ligase chain reaction (RT-LCR).

Northern blot analysis can be performed as described in Harada et al., *Cell* 63:303–312 (1990). Briefly, total RNA is prepared from a biological sample as described above. For the Northern blot, the RNA is denatured in an appropriate buffer (such as glyoxal/dimethyl sulfoxide/sodium phosphate buffer), subjected to agarose gel electrophoresis, and transferred onto a nitrocellulose filter. After the RNAs have been linked to the filter by a UV linker, the filter is prehybridized in a solution containing formamide, SSC, Denhardt's solution, denatured salmon sperm, SDS, and sodium phosphate buffer. CKβ-15 protein cDNA labeled according to any appropriate method (such as the $^{32}$P-multiprimed DNA labeling system (Amersham)) is used as probe. After hybridization overnight, the filter is washed and exposed to x-ray film. cDNA for use as probe according to the present invention is described in the sections above and will preferably at least 15 bp in length.

S1 mapping can be performed as described in Fujita et al., *Cell* 49:357–367 (1987). To prepare probe DNA for use in S1 mapping, the sense strand of above-described cDNA is used as a template to synthesize labeled antisense DNA. The antisense DNA can then be digested using an appropriate restriction endonuclease to generate further DNA probes of a desired length. Such antisense probes are useful for visualizing protected bands corresponding to the target mRNA (i.e., mRNA encoding the CKβ-15 protein). Northern blot analysis can be performed as described above.

Preferably, levels of mRNA encoding the CKβ-15 protein are assayed using the RT-PCR method described in Makino et al., *Technique* 2:295–301 (1990). By this method, the radioactivities of the "amplicons" in the polyacrylamide gel bands are linearly related to the initial concentration of the target mRNA. Briefly, this method involves adding total RNA isolated from a biological sample in a reaction mixture containing a RT primer and appropriate buffer. After incubating for primer annealing, the mixture can be supplemented with a RT buffer, dNTPs, DTT, RNase inhibitor and reverse transcriptase. After incubation to achieve reverse transcription of the RNA, the RT products are then subject to PCR using labeled primers. Alternatively, rather than labeling the primers, a labeled dNTP can be included in the PCR reaction mixture. PCR amplification can be performed in a DNA thermal cycler according to conventional techniques. After a suitable number of rounds to achieve amplification, the PCR reaction mixture is electrophoresed on a polyacrylamide gel. After drying the gel, the radioactivity of the appropriate bands (corresponding to the mRNA encoding the CKβ-15 protein) is quantified using an imaging analyzer. RT and PCR reaction ingredients and conditions, reagent and gel concentrations, and labeling methods are well known in the art. Variations on the RT-PCR method will be apparent to the skilled artisan.

Any set of oligonucleotide primers which will amplify reverse transcribed target mRNA can be used and can be designed as described in the sections above.

Assaying CKβ-15 protein levels in a biological sample can occur using any art-known method. Preferred for assaying CKβ-15 protein levels in a biological sample are antibody-based techniques. For example, CKβ-15 protein expression in tissues can be studied with classical immunohistological methods. In these, the specific recognition is provided by the primary antibody (polyclonal or monoclonal) but the secondary detection system can utilize fluorescent, enzyme, or other conjugated secondary antibodies. As a result, an immunohistological staining of tissue section for pathological examination is obtained. Tissues can also be extracted, e.g., with urea and neutral detergent, for the liberation of CKβ-15 protein for Western-blot or dot/slot assay (Jalkanen, M., et al., *J. Cell. Biol.* 101:976–985 (1985)); Jalkanen, M., et al., *J. Cell. Biol.* 105:3087–3096 (1987)). In this technique, which is based on the use of cationic solid phases, quantitation of CKβ-15 protein can be accomplished using isolated CKβ-15 protein as a standard. This technique can also be applied to body fluids. With these samples, a molar concentration of CKβ-15 protein will aid to set standard values of CKβ-15 protein content for different body fluids, like serum, plasma, urine, synovial fluid, spinal fluid, etc. The normal appearance of CKβ-15 protein amounts can then be set using values from healthy individuals, which can be compared to those obtained from a test subject.

Other antibody-based methods useful for detecting CKβ-15 protein levels include immunoassays, such as the enzyme linked immunosorbent assay (ELISA) and the radioimmunoassay (RIA). For example, CKβ-15 protein-specific monoclonal antibodies can be used both as an immunoadsorbent and as an enzyme-labeled probe to detect and quantify the CKβ-15 protein. The amount of CKβ-15 protein present in the sample can be calculated by reference to the amount present in a standard preparation using a linear regression computer algorithm. Such an ELISA for detecting a tumor antigen is described in Iacobelli et al., *Breast Cancer Research and Treatment* 11:19–30 (1988). In another ELISA assay, two distinct specific monoclonal antibodies can be used to detect CKβ-15 protein in a body fluid. In this assay, one of the antibodies is used as the immunoadsorbent and the other as the enzyme-labeled probe.

The above techniques may be conducted essentially as a "one-step" or "two-step" assay. The "one-step" assay involves contacting CKβ-15 protein with immobilized antibody and, without washing, contacting the mixture with the labeled antibody. The "two-step" assay involves washing before contacting the mixture with the labeled antibody. Other conventional methods may also be employed as suitable. It is usually desirable to immobilize one component of the assay system on a support, thereby allowing other components of the system to be brought into contact with the component and readily removed from the sample.

Suitable enzyme labels include, for example, those from the oxidase group, which catalyze the production of hydrogen peroxide by reacting with substrate. Glucose oxidase is particularly preferred as it has good stability and its substrate (glucose) is readily available. Activity of an oxidase label may be assayed by measuring the concentration of hydrogen peroxide formed by the enzyme-labeled antibody/substrate reaction. Besides enzymes, other suitable labels include radioisotopes, such as iodine ($^{125}$I, $^{121}$I), carbon ($^{14}$C), sulfur ($^{35}$S), tritium ($^{3}$H), indium ($^{112}$In), and technetium ($^{99m}$Tc), and fluorescent labels, such as fluorescein and rhodamine, and biotin.

In addition to assaying CKβ-15 protein levels in a biological sample obtained from an individual, CKβ-15 protein can also be detected in vivo by imaging. Antibody labels or markers for in vivo imaging of CKβ-15 protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A CKβ-15 protein-specific antibody or antibody portion which has been labeled with an appropriate detectable imaging moiety, such as a radioisotope (for example, $^{131}$I, $^{112}$In, $^{99m}$Tc), a radio-opaque substance, or a material detectable by nuclear magnetic resonance, is introduced (for example, parenterally, subcutaneously or intraperitoneally) into the mammal to be examined for a thymus disorder. It will be understood in the art that the size of the subject and the imaging system used will determine the quantity of imaging moieties needed to produce diagnostic images. In the case of a radioisotope moiety, for a human subject, the quantity of radioactivity injected will normally range from about 5 to 20 millicuries of $^{99m}$Tc. The labeled antibody or antibody portion will then preferentially accumulate at the location of cells which contain CKβ-15 protein. In vivo tumor imaging is described in S. W. Burchiel et al., "Immunopharmacokinetics of Radiolabeled Antibodies and Their Portions" (Chapter 13 in *Tumor Imaging: The Radiochemical Detection of Cancer*, eds., S. W. Burchiel and B. A. Rhodes, Masson Publishing Inc. (1982)).

CKβ-15-protein specific antibodies for use in the present invention can be raised against the intact CKβ-15 protein or an antigenic polypeptide portion thereof, which may presented together with a carrier protein, such as an albumin, to an animal system (such as rabbit or mouse) or, if it is long enough (at least about 25 amino acids), without a carrier.

As used herein, the term "antibody" (Ab) or "monoclonal antibody" (Mab) is meant to include intact molecules as well as antibody portions (such as, for example, Fab and F(ab')$_2$ portions) which are capable of specifically binding to CKβ-15 protein. Fab and F(ab')$_2$ portions lack the Fc portion of intact antibody, clear more rapidly from the circulation, and may have less non-specific tissue binding of an intact antibody (Wahl et al., *J. Nucl. Med.* 24:316–325 (1983)). Thus, these portions are preferred.

The antibodies of the present invention may be prepared by any of a variety of methods. For example, cells expressing the CKβ-15 protein or an antigenic portion thereof can be administered to an animal in order to induce the production of sera containing polyclonal antibodies. In a preferred method, a preparation of CKβ-15 protein is prepared and purified as described above to render it substantially free of natural contaminants. Such a preparation is then introduced into an animal in order to produce polyclonal antisera of greater specific activity.

In the most preferred method, the antibodies of the present invention are monoclonal antibodies (or CKβ-15 protein binding portions thereof). Such monoclonal antibodies can be prepared using hybridoma technology (Kohler et al., Nature 256:495 (1975); Kohler et al., Eur. J. Immunol. 6:511 (1976); Kohler et al., Eur. J. Immunol. 6:292 (1976); Hammerling et al., In: Monoclonal Antibodies and T-Cell Hybridomas, Elsevier, N.Y., pp. 563–681 (1981)). In general, such procedures involve immunizing an animal (preferably a mouse) with a CKβ-15 protein antigen or, more preferably, with a CKβ-15 protein-expressing cell. Suitable cells can be recognized by their capacity to bind anti-CKβ-15 protein antibody. Such cells may be cultured in any suitable tissue culture medium; however, it is preferable to culture cells in Earle's modified Eagle's medium supplemented with 10% fetal bovine serum (inactivated at about 56° C.), and supplemented with about 10 μg/l of nonessential amino acids, about 1,000 U/ml of penicillin, and about 100 μg/ml of streptomycin. The splenocytes of such mice are extracted and fused with a suitable myeloma cell line. Any suitable myeloma cell line may be employed in accordance with the present invention; however, it is preferable to employ the parent myeloma cell line (SP$_2$O), available from the American Type Culture Collection, Rockville, Md. After fusion, the resulting hybridoma cells are selectively maintained in HAT medium, and then cloned by limiting dilution as described by Wands et al. (Gastroenterology 80:225–232 (1981)). The hybridoma cells obtained through such a selection are then assayed to identify clones which secrete antibodies capable of binding the CKβ-15 antigen.

Alternatively, additional antibodies capable of binding to the CKβ-15 protein antigen may be produced in a two-step procedure through the use of anti-idiotypic antibodies. Such a method makes use of the fact that antibodies are themselves antigens, and therefore it is possible to obtain an antibody which binds to a second antibody. In accordance with this method, CKβ-15 protein specific antibodies are used to immunize an animal, preferably a mouse. The splenocytes of such an animal are then used to produce hybridoma cells, and the hybridoma cells are screened to identify clones which produce an antibody whose ability to bind to the CKβ-15 protein-specific antibody can be blocked by the CKβ-15 protein antigen. Such antibodies comprise anti-idiotypic antibodies to the CKβ-15 protein-specific antibody and can be used to immunize an animal to induce formation of further CKβ-15 protein-specific antibodies.

It will be appreciated that Fab and F(ab')$_2$ and other portions of the antibodies of the present invention may be used according to the methods disclosed herein. Such portions are typically produced by proteolytic cleavage, using enzymes such as papain (to produce Fab portions) or pepsin (to produce F(ab')$_2$ portions). Alternatively, CKβ-15 protein-binding portions can be produced through the application of recombinant DNA technology or through synthetic chemistry.

Where in vivo imaging is used to detect enhanced levels of CKβ-15 protein for diagnosis in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. See, for review, Morrison, Science 229:1202 (1985); Oi et al., BioTechniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985).

Further suitable labels for the CKβ-15 protein-specific antibodies of the present invention are provided below. Examples of suitable enzyme labels include malate dehydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, and acetylcholine esterase.

Examples of suitable radioisotopic labels include $^3$H, $^{111}$In, $^{125}$I, $^{131}$I, $^{32}$P, $^{35}$S, $^{14}$C, $^{51}$Cr, $^{57}$To, $^{58}$Co, $^{59}$Fe, $^{75}$Se, $^{152}$Eu, $^{90}$Y, $^{67}$Cu, $^{217}$Ci, $^{211}$At $^{212}$Pb, $^{47}$SC, $^{109}$Pd, etc. $^{111}$In is a preferred isotope where in vivo imaging is used since its avoids the problem of dehalogenation of the $^{125}$I or $^{131}$I-labeled monoclonal antibody by the liver. In addition, this radionucleotide has a more favorable gamma emission energy for imaging (Perkins et al., Eur. J. Nucl. Med. 10:296–301 (1985); Carasquillo et al., J. Nucl. Med. 28:281–287 (1987)). For example, $^{111}$In coupled to monoclonal antibodies with 1-(P-isothiocyanatobenzyl)-DPTA has shown little uptake in non-tumorous tissues, particularly the liver, and therefore enhances specificity of tumor localization (Esteban et al., J. Nucl. Med. 28:861–870 (1987)).

Examples of suitable non-radioactive isotopic labels include $^{157}$Gd, $^{55}$Mn, $^{162}$Dy, $^{52}$Tr, and $^{56}$Fe.

Examples of suitable fluorescent labels include an $^{152}$Eu label, a fluorescein label, an isothiocyanate label, a rhodamine label, a phycoerythrin label, a phycocyanin label, an allophycocyanin label, an o-phthaldehyde label, and a fluorescamine label.

Examples of suitable toxin labels include diphtheria toxin, ricin, and cholera toxin.

Examples of chemiluminescent labels include a luminal label, an isoluminal label, an aromatic acridinium ester label, an imidazole label, an acridinium salt label, an oxalate ester label, a luciferin label, a luciferase label, and an aequorin label.

Examples of nuclear magnetic resonance contrasting agents include heavy metal nuclei such as Gd, Mn, and Fe.

Typical techniques for binding the above-described labels to antibodies are provided by Kennedy et al. (Clin. Chim. Acta 70:1–31 (1976)), and Schurs et al. (Clin. Chim. Acta 81:140 (1977)). Coupling techniques mentioned in the latter are the glutaraldehyde method, the periodate method, the dimaleimide method, the m-maleimidobenzyl-N-hydroxysuccinimide ester method, all of which methods are incorporated by reference herein.

Chromosome Assays

The nucleic acid molecules of the present invention are also valuable for chromosome identification. The sequence is specifically targeted to and can hybridize with a particular location on an individual human chromosome. Moreover, there is a current need for identifying particular sites on the chromosome. Few chromosome making reagents based on actual sequence data (repeat polymorphisms) are presently available for marking chromosomal location. The mapping of DNAs to chromosomes according to the present invention is an important first step in correlating those sequences with genes associated with disease.

In certain preferred embodiments in this regard, the cDNA herein disclosed is used to clone genomic DNA of a CKβ-15 protein gene. This can be accomplished using a variety of well known techniques and libraries, which generally are available commercially. The genomic DNA then is used for in situ chromosome mapping using well known techniques for this purpose. Typically, in accordance with routine procedures for chromosome mapping, some trial and error may be necessary to identify a genomic probe that gives a good in situ hybridization signal.

In some cases, in addition, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified portion.

PCR mapping of somatic cell hybrids is a rapid procedure for assigning a particular DNA to a particular chromosome. Using the present invention with the same oligonucleotide primers, sublocalization can be achieved with panels of portions from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization ("FISH") of a cDNA clone to a metaphase chromosomal spread can be used to provide a precise chromosomal location in one step. This technique can be used with probes from the cDNA as short as 50 or 60 bp. For a review of this technique, see Verma et al., HUMAN CHROMOSOMES: A MANUAL OF BASIC TECHNIQUES, Pergamon Press, New York (1988).

Once a sequence has been mapped to a precise chromosomal location, the physical position of the sequence on the chromosome can be correlated with genetic map data. Such data are found, for example, in V. McKusick, MENDELIAN INHERITANCE IN MAN, available on-line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

Treatment of Thymus-Related Disorders

As noted above, unlike other known CC cytokines, CKβ-15 has been shown to be expressed only in the thymus. Therefore, CKβ-15 is particularly active in modulating activities of monocytes in the thymus, particularly those of early thymocytes, such as the activities described above in relation to the description of a "polypeptide having CKβ-15 activity." Given the thymocyte activities modulated by CKβ-15, it is readily apparent that a substantially altered (increased or decreased) level of expression of CKβ-15 in an individual compared to the standard or "normal" level produces pathological conditions such as those described above in relation to diagnosis of thymus-related disorders. It will also be appreciated by one of ordinary skill that, since the CKβ-15 protein of the invention is translated with a leader peptide suitable for secretion of the mature protein from the cells which express CKβ-15, when CKβ-15 protein (particularly the mature form) is added from an exogenous source to cells, tissues or the body of an individual, the protein will exert its modulating activities on any of its target cells of that individual. Therefore, it will be appreciated that conditions caused by a decrease in the standard or normal level of CKβ-15 activity in an individual, particularly disorders of the thymus, can be treated be administration of CKβ-15 protein. Thus, the invention also provides a method of treatment of an individual in need of an increased level of CKβ-15 activity comprising administering to such an individual a pharmaceutical composition comprising an amount of an isolated CKβ-15 polypeptide of the invention, particularly a mature form of the CKβ-15 protein of the invention, effective to increase the CKβ-15 activity level in such an individual.

In addition, since the CKβ-15 protein suppresses myeloid cell growth when administered to an individual, the invention provides methods for suppressing myeloid cell proliferation in an individual, which involve administering a myelosuppressive amount of CKβ-15 either alone or together with one or more chemokines selected from the group consisting of Macrophage Inflammatory Protein-1α (MIP-1α), Macrophage Inflammatory Protein-2α (MIP-2α), Platelet Factor 4 (PF4), Interleukin-8 (IL-8), Macrophage Chemotactic and Activating Factor (MCAF), and Macrophage Inflammatory Protein-Related Protein-2 (MRP-2). The myelosuppressive compositions of the present invention thus provide myeloprotective effects and are useful in conjunction with therapies that have an adverse affect on myeloid cells. This is because the myelosuppressive compositions of the present invention place myeloid cells in a slow-cycling state thereby providing protection against cell damage caused by, for example, radiation therapy or chemotherapy using cell-cycle active drugs, such as cytosine arabinoside and hydroxyurea.

The myelosuppressive pharmaceutical compositions of the present invention are also useful in the treatment of leukemia, which causes a hyperproliferative myeloid cell state. Thus, the invention further provides methods for treating leukemia, which involve administering to a leukemia patient a myelosuppressive amount of CKβ-15 either alone or together with one or more chemokines selected from the group consisting of MIP-la, MIP-2a, PF4, IL-8, MCAF, and MRP-2.

By "suppressing myeloid cell proliferation" is intended decreasing the cell proliferation of myeloid cells and/or increasing the percentage of myeloid cells in the slow-cycling phase. As above, by "individual" is intended mammalian individuals, preferably humans. Preincubation of the myelosuppressive compositions of the present invention with acetonitrile (ACN) significantly enhances the specific activity of these chemokines for suppression of myeloid progenitor cells. Thus, preferably, prior to administration, the myelosuppresive compositions of the present invention are pretreated with ACN as described in Broxmeyer H. E., et al., *Ann-Hematol.* 71(5):23546(1995) and PCT Publication WO 94/13321, the entire disclosures of which are hereby incorporated herein by reference.

The myelosuppressive compositions of the present invention may be used in combination with a variety of chemotherapeutic agents including alkylating agents such as nitrogen mustards, ethylenimines, methylmelamines, alkyl sulfonates, nitrosuoureas, and triazenes; antimetabolites such as folic acid analogs, pyrimidine analogs, in particular fluorouracil and cytosine arabinoside, and purine analogs; natural products such as vinca alkaloids, epipodophyllotoxins, antibiotics, enzymes and biological response modifiers; and miscellaneous products such as platinum coordination complexes, anthracenedione, substituted urea such as hydroxyurea, methyl hydrazine derivatives, and adrenocorticoid suppressant.

Chemotherapeutic agents can be administered at known concentrations according to known techniques. The myelosuppressive compositions of the present invention can be co-administered with a chemotherapeutic agent, or administered separately, either before or after chemotherapeutic administration.

Certain chemokines, such as MIP-1β, MIP-2β and GRO-α, inhibit (at least partially block) the myeloid suppressive affects of the myelosuppresive compositions of the present invention. Thus, in a further embodiment, the invention provides methods for inhibiting myelosuppression, which involves administering an effective amount of a myelosuppressive inhibitor selected from the group consisting of MIP-1β, MIP-2β and GRO-α to a mammal previously exposed to the myelosuppresive agent CKβ-15 either alone or together with one or more of MIP-1α, MIP-2α, PF4, IL-8, MCAF, and MRP-2.

One of ordinary skill will appreciate that effective amounts of the CKβ-15 polypeptides for treating an individual in need of an increased level of CKβ-15 activity (including amounts of CKβ-15 polypeptides effective for myelosuppression with or without myelosuppressive agents or myelosuppressive inhibitors) can be determined empirically for each condition where administration of CKβ-15 is indicated. The polypeptide having CKβ-15 activity my be administered in pharmaceutical compositions in combination with one or more pharmaceutically acceptable excipients. It will be understood that, when administered to a human patient, the total daily usage of the pharmaceutical compositions of the present invention will be decided by the attending physician within the scope of sound medical judgment. The specific therapeutically effective dose level for any particular patient will depend upon a variety of factors including the type and degree of the response to be achieved; the specific composition an other agent, if any, employed; the age, body weight, general health, sex and diet of the patient; the time of administration, route of administration, and rate of excretion of the composition; the duration of the treatment; drugs (such as a chemotherapeutic agent) used in combination or coincidental with the specific composition; and like factors well known in the medical arts.

For example, satisfactory results are obtained by oral administration of a polypeptide having CKβ-15 activity in dosages on the order of from 0.05 to 10 mg/kg/day, preferably 0.1 to 7.5 mg/kg/day, more preferably 0.1 to 2 mg/kg/day, administered once or, in divided doses, 2 to 4 times per day. On administration parenterally, for example by i.v. drip or infusion, dosages on the order of from 0.01 to 5 mg/kg/day, preferably 0.05 to 1.0 mg/kg/day and more preferably 0.1 to 1.0 mg/kg/day can be used Suitable daily dosages for patients are thus on the order of from 2.5 to 500 mg p.o., preferably 5 to 250 mg p.o., more preferably 5 to 100 mg p.o., or on the order of from 0.5 to 250 mg i.v., preferably 2.5 to 125 mg i.v. and more preferably 2.5 to 50 mg i.v.

Dosaging may also be arranged in a patient specific manner to provide a predetermined concentration of an CKβ-15 activity in the blood, as determined by an RIA technique, for instance. Thus patient dosaging may be adjusted to achieve regular on-going trough blood levels, as measured by RIA, on the order of from 50 to 1000 ng/ml, preferably 150 to 500 ng/ml.

Pharmaceutical compositions of the invention may be administered orally, rectally, parenterally, intracistemally, intravaginally, intraperitoneally, topically (as by powders, ointments, drops or transdermal patch), bucally, or as an oral or nasal spray. By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

Pharmaceutical compositions of the present invention for parenteral injection can comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and non-aqueous carriers, diluents, solvents or vehicles include water, ethanol, polyols (such as glycerol, propylene glycol, polyethylene glycol, and the like), carboxymethylceuulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

The compositions of the present invention may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the pharmaceutical composition, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsuled matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compounds are mixed with at least one item pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcerulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f)-absorption accelerators such as quaternary ammonium compounds, g) wetting agents such as, for example, cetyl alcohol and glycerol monostearate, h)-absorbents such as kaolin and bentonite clay, and I) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isoptopyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

The active polypeptide can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to the agent or inhibitor, stabilizers, preservatives, excipients, and the like. The preferred lipids are the phospholipids and the phosphatidyl cholates (lecithins), both natural and synthetic. Methods to form liposomes are known in the art. See, for example, Prescott, Ed., *Methods in Cell Biology*, Volume XIV, Academic Press, New York, N.Y. (1976), p. 33 et seq.

Having generally described the invention, the same will be more readily understood by reference to the following examples, which are provided by way of illustration and are not intended as limiting.

EXAMPLES

Example 1

Expression and Purification of CKβ-15 in *E. coli*

The DNA sequence encoding the mature CKβ-15 protein in the deposited cDNA clone was amplified using PCR oligonucleotide primers specific to the amino terminal sequences of the CKβ-15 protein and to vector sequences 3' to the gene. Additional nucleotides containing restriction sites to facilitate cloning were added to the 5' and 3' sequences respectively.

The 5' oligonucleotide primer had the sequence 5' GCC GTCGAC GTC CAC ACC CAA GGT GTC 3' [SEQ ID NO:4] containing the underlined SalI restriction site, which encodes 18 nucleotides of the CKβ-15 protein coding sequence in FIG. 1 [SEQ ID NO:1] beginning immediately after the signal peptide.

The 3' primer had the sequence 5' GCC TCTAGA GGA GCC CAG AAA TGA GCC GGC 3' [SEQ ID NO:5] containing the underlined XbaI restriction site followed by 21 nucleotides complementary to the last 21 nucleotides immediately after the CKβ-15 protein coding sequence in FIG. 1.

The restriction sites were convenient to restriction enzyme sites in the bacterial expression vector pD10 (pQE9), which were used for bacterial expression in these examples. (Qiagen, Inc. 9259 Eton Avenue, Chatsworth, Calif., 91311). [pD10]pQE9 encodes ampicillin antibiotic resistance ("Amp'") and contains a bacterial origin of replication ("ori"), an IPTG inducible promoter, a ribosome binding site ("RBS"), a 6-His tag and restriction enzyme sites.

The amplified CKβ-15 protein DNA and the vector pQE9 both were digested with SalI and XbaI and the digested DNAs were then ligated together. Insertion of the CKβ-15 protein DNA into the restricted pQE9 vector placed the CKβ-15 protein coding region downstream of and operably linked to the vector's IPTG-inducible promoter and in-frame with an initiating AUG appropriately positioned for translation of CKβ-15 protein.

The ligation mixture was transformed into competent *E. coli* cells using standard procedures. Such procedures are described in Sambrook et al., MOLECULAR CLONING: A LABORATORY MANUAL, 2nd Ed.; Cold Spring Harbor Laboratory Press, Cold Spring Harbor, N.Y. (1989). *E. coli* strain M15/rep4, containing multiple copies of the plasmid pREP4, which expresses lac repressor and confers kanamycin resistance ("Kan'"), was used in carrying out the illustrative example described here. This strain, which is only one of many that are suitable for expressing CKβ-15 protein, is available commercially from Qiagen.

Transformants were identified by their ability to grow on LB plates in the presence of ampicillin and kanamycin. Plasmid DNA was isolated from resistant colonies and the identity of the cloned DNA was confirmed by restriction analysis.

Clones containing the desired constructs were grown overnight ("O/N") in liquid culture in LB media supplemented with both ampicillin (100 µg/ml) and kanamycin (25 µg/ml).

The O/N culture is used to inoculate a large culture, at a dilution of approximately 1:100 to 1:250. The cells are grown to an optical density at 600 nm ("OD600") of between 0.4 and 0.6. Isopropyl-B-D-thiogalactopyranoside ("IPTG") is then added to a final concentration of 1 mM to induce transcription from lac repressor sensitive promoters, by inactivating the lacI repressor. Cells subsequently are incubated further for 3 to 4 hours. Cells then are harvested by centrifugation and disrupted, by standard methods. Inclusion bodies are purified from the disrupted cells using routine collection techniques, and protein is solubilized from the inclusion bodies into 8M urea. The 8M urea solution containing the solubilized protein is passed over a PD-10 column in 2 × phosphate-buffered saline ("PBS"), thereby removing the urea, exchanging the buffer and refolding the protein. The protein is purified by a further step of chromatography to remove endotoxin. Then, it is sterile filtered. The sterile filtered protein preparation is stored in 2×PBS at a concentration of 95 µ/ml.

Analysis of the preparation by standard methods of polyacrylamide gel electrophoresis reveals that the preparation contains about 95% monomer CKβ-15 protein having the expected molecular weight of approximately 16.7 kDa.

Example 2

Cloning and Expression of CKβ-15 Protein in a Baculovirus Expression System

The cDNA sequence encoding the full length CKβ-15 protein in the deposited clone is amplified using PCR oligonucleotide primers corresponding to the 5' and 3' sequences of the gene:

The 5' primer has the sequence 5' GCC TCTAGA GCC ATC ATG AAC CTG TGG CTC CTG GCC 3' [SEQ ID NO:6] containing the underlined XbaI restriction enzyme site followed by 21 bases of the sequence of CKβ-15 protein in FIG. 1. Inserted into an expression vector, as described below, the 5' end of the amplified fragment encoding CKβ-15 provides an efficient signal peptide. An efficient signal for initiation of translation in eukaryotic cells, as described by Kozak, M., J. Mol. Biol. 196: 947–950 (1987) is appropriately located in the vector portion of the construct.

The 3' primer has the sequence 5' GCC TCTAGA GGA GCC CAG AAA TGA CCC GGC 3' [SEQ ID NO:7] containing the underlined XbaI restriction site followed by nucleotides complementary to the last 21 nucleotides of the CKβ-15 coding sequence set out in FIG. 1.

The amplified fragment is isolated from a 1% agarose gel using a commercially available kit ("Geneclean," BIO 101 Inc., La Jolla, Calif.). The fragment then is digested with XbaI and again is purified on a 1% agarose gel. This fragment is designated herein F2.

The vector pA2 is used to express the CKβ-15 protein in the baculovirus expression system, using standard methods, as described in Summers et al, A MANUAL OF METHODS FOR BACULOVIRUS VECTORS AND INSECT CELL CULTURE PROCEDURES, Texas Agricultural Experimental Station Bulletin No. 1555 (1987). This expression vector contains the strong polyhedrin promoter of the *Autographa californica* nuclear polyhedrosis virus (AcMNPV) followed by convenient restriction sites such as BamHI and Asp718. The polyadenylation site of the simian virus 40 ("SV40") is used for efficient polyadenylation. For easy selection of recombinant virus, the plasmid contains the beta-galactosidase gene from *E. coli* under control of a weak *Drosophila* promoter in the same orientation, followed by the polyadenylation signal of the polyhedrin gene. The inserted genes are flanked on both sides by viral sequences for cell-mediated homologous recombination with wild-type viral DNA to generate viable virus that express the cloned polynucleotide.

Many other baculovirus vectors could be used in place of pA2, such as pAc373, pVL941 and pAcIM1 provided, as those of skill readily will appreciate, that construction provides appropriately located signals for transcription, translation, trafficking and the like, such as an in-frame AUG and a signal peptide, as required. Such vectors are described in Luckow et al., Virology 170:31–39, among others.

The plasmid is digested with the restriction enzyme XbaI and then is dephosphorylated using calf intestinal phosphatase, using routine procedures known in the art. The DNA is then isolated from a 1% agarose gel using a commercially available kit ("Geneclean" BIO 101 Inc., La Jolla, Calif.). This vector DNA is designated herein "V2".

Fragment F2 and the dephosphorylated plasmid V2 are ligated together with T4 DNA ligase. *E. coli* HB101 cells are transformed with ligation mix and spread on culture plates. Bacteria are identified that contain the plasmid with the human CKβ-15 gene by digesting DNA from individual colonies using XbaI and then analyzing the digestion product by gel electrophoresis. The sequence of the cloned fragment is confirmed by DNA sequencing. This plasmid is designated herein pBacCKβ-15.

5 µg of the plasmid pBacCKβ-15 is co-transfected with 1.0 µg of a commercially available linearized baculovirus DNA ("BaculoGold™ baculovirus DNA", Pharmingen, San Diego, Calif.), using the lipofection method described by Feigner et al., Proc. Natl. Acad. Sci. USA 84: 7413–7417 (1987). 1 µg of BaculoGold™ virus DNA and 5 µg of the plasmid pBacCKβ-15 are mixed in a sterile well of a microtiter plate containing 50 µl of serum-free Grace's medium (Life Technologies Inc., Gaithersburg, Md.). Afterwards 10 µl Lipofectin plus 90 µl Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is rocked back and forth to mix the newly added solution. The plate is then incubated for 5 hours at 27° C. After S hours the transfection solution is removed from the plate and 1 ml of Grace's insect medium supplemented with 10% fetal calf serum is added. The plate is put back into an incubator and cultivation is continued at 27° C. for four days.

After four days the supernatant is collected and a plaque assay is performed, as described by Summers and Smith, cited above. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10).

Four days after serial dilution, the virus is added to the cells. After appropriate incubation, blue stained plaques are picked with the tip of an Eppendorf pipette. The agar containing the recombinant viruses is then resuspended in an Eppendorf tube containing 200 μl of Grace's medium. The agar is removed by a brief centrifugation and the supernatant containing the recombinant baculovirus is used to infect Sf9 cells seeded in 35 mm dishes. Four days later the supernatants of these culture dishes are harvested and then they are stored at 4° C. A clone containing properly inserted HESSB I, II and III is identified by DNA analysis including restriction mapping and sequencing. This is designated herein as V-CKβ-15.

Sf9 cells are grown in Grace's medium supplemented with 10% heat-inactivated FBS. The cells are infected with the recombinant baculovirus V-CKβ-15 at a multiplicity of infection ("MOI") of about 2 (about 1 to about 3). Six hours later the medium is removed and is replaced with SF900 II medium minus methionine and cysteine (available from Life Technologies Inc., Gaithersburg). 42 hours later, 5 μCi of $^{35}$S-methionine and 5 μCi $^{35}$S-cysteine (available from Amersham) are added. The cells are further incubated for 16 hours and then they are harvested by centrifugation, lysed and the labeled proteins are visualized by SDS-PAGE and autoradiography.

Example 3

Expression in Mammalian Cells (COS)

The expression plasmid, pCKβ-15 HA, is made by cloning a cDNA encoding CKβ-15 into the expression vector pcDNAI/Amp (which can be obtained from Invitrogen, Inc.).

The expression vector pcDNAIamp contains: (1) an *E.coli* origin of replication effective for propagation in *E. coli* and other prokaryotic cells; (2) an ampicillin resistance gene for selection of plasmid-containing prokaryotic cells; (3) an SV40 origin of replication for propagation in eukaryotic cells; (4) a CMV promoter, a polylinker, an SV40 intron, and a polyadenylation signal arranged so that a cDNA conveniently can be placed under expression control of the CMV promoter and operably linked to the SV40 intron and the polyadenylation signal by means of restriction sites in the polylinker.

A DNA fragment encoding the entire CKβ-15 precursor and an HA tag fused in frame to its 3' end is cloned into the polylinker region of the vector so that recombinant protein expression is directed by the CMV promoter. The HA tag corresponds to an epitope derived from the influenza hemagglutinin protein described by Wilson et al., Cell 37: 767 (1984). The fusion of the HA tag to the target protein allows easy detection of the recombinant protein with an antibody that recognizes the HA epitope.

The plasmid construction strategy is as follows.

The CKβ-15 cDNA of the deposited clone is amplified using primers that contain convenient restriction sites, much as described above regarding the construction of expression vectors for expression of CKβ-15 in *E. coli*. To facilitate detection, purification and characterization of the expressed CKβ-15, one of the primers contains a hemagglutinin tag ("HA tag") as described above.

Suitable primers include that following, which are used in this example. The 5' primer, containing the underlined HindIII site, an AUG start codon and 6 codons of the 5' coding region has the following sequence: 5' GCG AAGCTT ATG AAC CTG TGG CTC CTG GCC 3' [SEQ ID NO:8].

The 3' primer, containing the underlined XhoI site, a stop codon, 9 codons thereafter forming the hemagglutinin HA tag, and 22 bp of 3' coding sequence (at the 3' end) has the following sequence: 5' GCG CTCGAG TCA AGC GTA GTC TGG GAC GTC GTA TOG OTA CAG TCC TGA ATT AGC TGA TAT C3' [SEQ ID NO:9].

The PCR amplified DNA fragment and the vector, pcDNAI/Amp, are digested with HindIII and XhoI and then ligated. The ligation mixture is transformed into *E. coli* strain SURE (available from Stratagene Cloning Systems, 11099 North Torrey Pines Road, La Jolla, Calif. 92037) the transformed culture is plated on ampicillin media plates which then are incubated to allow growth of ampicillin resistant colonies. Plasmid DNA is isolated from resistant colonies and examined by restriction analysis and gel sizing for the presence of the CKβ-15-encoding fragment.

For expression of recombinant CKβ-15, COS cells are transfected with an expression vector, as described above, using DEAE-DEXTRAN, as described, for instance, in Sambrook et al., MOLECULAR CLONING: A LABORATORY MANUAL, Cold Spring Laboratory Press, Cold Spring Harbor, N.Y. (1989). Cells are incubated under conditions for expression of CKβ-15 by the vector.

Expression of the CKβ-15 HA fusion protein is detected by radiolabelling and immunoprecipitation, using methods described in, for example Harlow et al., ANTIBODIES: A LABORATORY MANUAL, 2nd Ed.; Cold Spring Harbor Laboratory Press, Cold Spring Harbor, N.Y. (1988). To this end, two days after transfection, the cells are labeled by incubation in media containing $^{35}$S-cysteine for 8 hours. The cells and the media are collected, and the cells are washed and the lysed with detergent-containing RIPA buffer: 150 mM NaCl, 1% NP-40, 0.1% SDS, 1% NP-40, 0.5% DOC, 50 mM TRIS, pH 7.5, as described by Wilson et al. cited above. Proteins are precipitated from the cell lysate and from the culture media using an HA-specific monoclonal antibody. The precipitated proteins then are analyzed by SDS-PAGE gels and autoradiography. An expression product of the expected size is seen in the cell lysate, which is not seen in negative controls.

Example 4

Tissue Distribution of CKβ-15 Protein Expression

Northern blot analysis was carried out to examine the levels of expression of CKβ-15 protein in human tissues, using methods described by, among others, Sambrook et al, cited above. PolyA$^+$ was purchased form Clontech (1020 East Meadow Circle, Palo Alto, Calif. 94303).

About 1 μg of PolyA$^+$ RNA was size resolved by electrophoresis through a 1% agarose gel under strongly denaturing conditions. RNA was blotted from the gel onto a nylon filter, and the filter then was prepared for hybridization to a detectably labeled polynucleotide probe.

As a probe to detect mRNA that encodes CKβ-15 protein, the antisense strand of the coding region of the cDNA insert in the deposited clone was labeled to a high specific activity. The cDNA was labeled by primer extension, using the Prime-It kit, available from Stratagene. The reaction was carried out using 50 ng of the cDNA, following the standard reaction protocol as recommended by the supplier. The labeled polynucleotide was purified away from other labeled reaction components by column chromatography using a Select-G-50 column, obtained from 5-Prime–3-Prime, Inc. of 5603 Arapahoe Road, Boulder, Colo. 80303.

The labeled probe was hybridized to the filter, at a concentration of 1,000,000 cpm/ml, as described in Kreider et al., Molecular and Cellular Biology, Sept. 1990, pp. 4846–4853. Thereafter the probe solution was drained and the filter was washed twice at room temperature and twice at 65° C. with 0.1×SSC, 0.1% SDS. The filter then was then dried and exposed to film at −70° C. overnight with an intensifying screen. The results of a typical Northern blot using the CKβ-15 cDNA probe are shown in FIG. 3.

Example 5

Gene Therapeutic Expression of Human CKβ-15 Protein

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature overnight. After 24 hours at room temperature, the flask is inverted—the chunks of tissue remain fixed to the bottom of the flask—and fresh media is added (e.g., Ham's F12 media, with 10% FBS, penicillin and streptomycin). The tissue is then incubated at 37° C. for approximately one week. At this time, fresh media is added and subsequently changed every several days. After an additional two weeks in culture, a monolayer of fibroblasts emerges. The monolayer is trypsinized and scaled into larger flasks.

A vector for gene therapy is digested with restriction enzymes for cloning a portion to be expressed. The digested vector is treated with calf intestinal phosphatase to prevent self-ligation. The dephosphorylated, linear vector is fractionated on an agarose gel and purified.

CKβ-15 protein cDNA capable of expressing active CKβ-15 protein, is isolated. The ends of the portion are modified, if necessary, for cloning into the vector. For instance, 5" overhanging may be treated with DNA polymerase to create blunt ends. 3' overhanging ends may be removed using S1 nuclease. Linkers may be ligated to blunt ends with T4 DNA ligase.

Equal quantities of the Moloney murine leukemia virus linear backbone and the CKβ-15 protein portion are mixed together and joined using T4 DNA ligase. The ligation mixture is used to transform *E. coli* and the bacteria are then plated onto agar-containing kanamycin. Kanamycin phenotype and restriction analysis confirm that the vector has the properly inserted gene.

Packaging cells are grown in tissue culture to confluent density in Dulbecco's Modified Eagles Medium (DMEM) with 10% calf serum (CS), penicillin and streptomycin. The vector containing the CKβ-15 protein gene is introduced into the packaging cells by standard techniques. Infectious viral particles containing the CKβ-15 protein gene are collected from the packaging cells, which now are called producer cells.

Fresh media is added to the producer cells, and after an appropriate incubation period media is harvested from the plates of confluent producer cells. The media, containing the infectious viral particles, is filtered through a Millipore filter to remove detached producer cells. The filtered media then is used to infect fibroblast cells. Media is removed from a sub-confluent plate of fibroblasts and quickly replaced with the filtered media. Polybrene (Aldrich) may be included in the media to facilitate transduction. After appropriate incubation, the media is removed and replaced with fresh media. If the titer of virus is high, then virtually all fibroblasts will be infected and no selection is required. If the titer is low, then it is necessary to use a retroviral vector that has a selectable marker, such as neo or his, to select out transduced cells for expansion.

Transformed fibroblasts then may be injected into rats, either alone or after having been grown to confluence on microcarrier beads, such as cytodex 3 beads. The injected fibroblasts produce CKβ-15 protein product, and the biological actions of the protein are conveyed to the host.

It will be clear that the invention may be practiced otherwise than as particularly described in the foregoing description and examples.

Numerous modifications and variations of the present invention are possible in light of the above teachings and, therefore, are within the scope of the appended claims.

The disclosures of all patents, patent applications, and publications referred to herein are hereby incorporated by reference.

What is claimed is:

1. An isolated chemokine β-15 polypeptide comprising an amino acid sequence selected from the group consisting of:
    (a) amino acids −20 to 129 of SEQ ID NO:2;
    (b) amino acids −19 to 129 of SEQ ID NO:2;
    (c) amino acids 1 to 129 of SEQ ID NO:2;
    (d) the amino acid sequence of the complete chemokine β-15 polypeptide having the amino acid sequence encoded by the cDNA contained in ATCC Deposit No. 97519; and
    (e) the amino acid sequence of the mature chemokine β-15 polypeptide having the amino acid sequence encoded by the cDNA contained in ATCC Deposit No. 97519.

2. The isolated chemokine β-15 polypeptide of claim 1, wherein said amino acid sequence is (a).

3. The isolated chemokine β-15 polypeptide of claim 1, wherein said amino acid sequence is (b).

4. The isolated chemokine β-15 polypeptide of claim 1, wherein said amino acid sequence is (c).

5. The isolated chemokine β-15 polypeptide of claim 1, wherein said amino acid sequence is (d).

6. The isolated chemokine β-15 polypeptide of claim 1, wherein said amino acid sequence is (e).

7. The isolated chemokine β-15 polypeptide of claim 1, wherein the amino acid sequence further comprises a heterologous polypeptide.

8. The isolated chemokine β-15 polypeptide of claim 1, wherein said isolated chemokine β15 polypeptide is glycosylated.

9. An isolated chemokine β-15 protein produced by the method comprising:
    (a) expressing the polypeptide of claim 1 by a cell, wherein the cell comprises a polynucleotide encoding said polypeptide; and
    (b) recovering said protein.

10. A composition comprising the isolated chemokine β-15 polypeptide of claim 1 and a carrier.

11. An isolated chemokine β-15 polypeptide consisting of an amino acid sequence selected from the group consisting of:
    (a) an amino acid sequence consisting of at least 30 contiguous amino acids of SEQ ID NO:2;
    (b) an amino acid sequence consisting of at least 50 contiguous amino acids of SEQ ID NO:2;
    (c) an amino acid sequence consisting of at least 30 contiguous amino acids of the amino acid sequence encoded by the cDNA contained in ATCC Deposit No. 97519; and
    (d) an amino acid sequence consisting of at least 50 contiguous amino acids of the amino acid sequence encoded by the cDNA contained in ATCC Deposit No. 97519.

12. The isolated chemokine β-15 polypeptide of claim 11, wherein said amino acid sequence is (a).

13. The isolated chemokine β-15 polypeptide of claim 11, wherein said amino acid sequence is (b).

14. The isolated chemokine β-15 polypeptide of claim 11, wherein said amino acid sequence is (c).

15. The isolated chemokine β-15 polypeptide of claim 11, wherein said amino acid sequence is (d).

16. The isolated chemokine β-15 polypeptide of claim 11, wherein the amino acid sequence further comprises a heterologous polypeptide.

17. The isolated chemokine β-15 polypeptide of claim 11, wherein said isolated chemokine β-15 polypeptide is glycosylated.

18. An isolated chemokine β-15 protein produced by the method comprising:
    (a) expressing the polypeptide of claim 11 by a cell, wherein the cell comprises a polynucleotide encoding said polypeptide; and
    (b) recovering said protein.

19. A composition comprising the isolated chemokine β-15 polypeptide of claim 11 and a carrier.

20. An isolated chemokine β-15 polypeptide comprising an amino acid sequence at least 95% identical to an amino acid sequence selected from the group consisting of:
    (a) amino acids −20 to 129 of SEQ ID NO:2;
    (b) amino acids 1 to 129 of SEQ ID NO:2;
    (c) the amino acid sequence of the complete chemokine β-15 polypeptide having the amino acid sequence encoded by the cDNA contained in ATCC Deposit No. 97519;
    (d) the amino acid sequence of the mature chemokine β-15 polypeptide having the amino acid sequence encoded by the cDNA contained in ATCC Deposit No. 97519;
wherein said isolated chemokine β-15 polypeptide stimulates thymocyte proliferation.

21. The isolated chemokine β-15 polypeptide of claim 20, wherein said amino acid sequence is (a).

22. The isolated chemokine β-15 polypeptide of claim 20, wherein said amino acid sequence is (b).

23. The isolated chemokine β-15 polypeptide of claim 20, wherein said amino acid sequence is (c).

24. The isolated chemokine β-15 polypeptide of claim 20, wherein said amino acid sequence is (d).

25. The isolated chemokine β-15 polypeptide of claim 20, wherein the amino acid sequence further comprises a heterologous polypeptide.

26. The isolated chemokine β-15 polypeptide of claim 20, wherein said isolated chemokine β-15 polypeptide is glycosylated.

27. An isolated chemokine β-15 protein produced by the method comprising:
    (a) expressing the polypeptide of claim 20 by a cell, wherein the cell comprises a polynucleotide encoding said polypeptide; and
    (b) recovering said protein.

28. A composition comprising the isolated chemokine β-15 polypeptide of claim 20 and a carrier.

* * * * *